(12) United States Patent
Aguiar et al.

(10) Patent No.: US 11,641,817 B2
(45) Date of Patent: May 9, 2023

(54) DEVICE AND METHOD FOR POLLINATING PLANTS

(71) Applicant: Monsanto Technology LLC, St. Louis, MO (US)

(72) Inventors: Diego Almeida Aguiar, Paracatu (BR); Eric L. Borrowman, St. Peters, MO (US); Diego Campos, Paracatu (BR); Amanuel G. Ghebretinsae, Chesterfield, MO (US); Jeffrey L. Kohne, Kirkwood, MO (US); Aldo Barbosa Lima, Paracatu (BR); Jason T. Mitchell, St. Charles, MO (US); Antonio Carlos Santos, Helena (BR); Isaías Segovia, Lima (PE); Gretchen E. Spiess, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 327 days.

(21) Appl. No.: 16/476,508

(22) PCT Filed: Jan. 5, 2018

(86) PCT No.: PCT/US2018/012565
§ 371 (c)(1),
(2) Date: Jul. 8, 2019

(87) PCT Pub. No.: WO2018/129302
PCT Pub. Date: Jul. 12, 2018

(65) Prior Publication Data
US 2019/0364753 A1    Dec. 5, 2019

Related U.S. Application Data

(60) Provisional application No. 62/443,240, filed on Jan. 6, 2017.

(51) Int. Cl.
*A01H 1/02* (2006.01)
*A01G 22/00* (2018.01)
*A01G 7/06* (2006.01)

(52) U.S. Cl.
CPC ........... *A01H 1/027* (2021.01); *A01G 7/06* (2013.01); *A01G 22/00* (2018.02)

(58) Field of Classification Search
CPC . A01G 22/00; A01G 1/00; A01G 7/00; A01G 7/06; A01H 1/00; A01H 1/02; A01H 1/021
See application file for complete search history.

(56) References Cited

U.S. PATENT DOCUMENTS 1,306,209 A * 6/1919 Williams ............... A01H 1/027
47/1.41
1,438,803 A 12/1922 Williams
(Continued)

FOREIGN PATENT DOCUMENTS

| CN | 102422807 A | 4/2012 |
| FR | 2979798 B1 | 3/2013 |
| WO | 2016/085355 A1 | 6/2016 |

OTHER PUBLICATIONS

International Search Report and Written Opinion for PCT/US18/12565, dated Jan. 5, 2018, 17 pages, Alexandria, Virginia.
(Continued)

*Primary Examiner* — Ebony E Evans
(74) *Attorney, Agent, or Firm* — Harness, Dickey & Pierce, P.L.C.

(57) ABSTRACT

A pollinating device for pollinating crop plants includes a base mountable on a carriage. At least one pollination unit is mounted on the base and includes a pollen-releasing apparatus configured to release pollen from male flowers of the plants and at least one nozzle for directing fluid along a flow path for delivering at least some of the released pollen (Continued)

to the pollen-receiving rows of crop plants. Certain pollinating devices include multiple pollination units spaced apart along a width of the base. Some pollination units include at least two opposing nozzles. Plants are pollinated by driving the carriage along a field and directing air from the nozzles over the pollen born by some plants to deliver the pollen to female flowers of other plants in the field.

24 Claims, 13 Drawing Sheets

(56) References Cited

U.S. PATENT DOCUMENTS

| | | | | |
|---|---|---|---|---|
| 3,584,787 | A | 6/1971 | Thomason | |
| 4,048,911 | A | 9/1977 | Petersen | |
| 4,087,937 | A * | 5/1978 | Meader | A01H 1/027<br>47/1.41 |
| 4,292,651 | A | 9/1981 | Kretz et al. | |
| 4,922,651 | A | 5/1990 | Atkinson | |
| 5,956,897 | A * | 9/1999 | Takashima | A01G 31/00<br>47/60 |
| 2011/0179982 | A1 | 7/2011 | Faulring | |
| 2013/0118066 | A1 * | 5/2013 | Cope | A01H 1/027<br>47/1.41 |
| 2021/0045306 | A1 * | 2/2021 | Baldet | A01H 1/027 |

OTHER PUBLICATIONS

European Search Report for 18736419.5, dated Aug. 3, 2020, 6 pages, Munich, Germany.

* cited by examiner

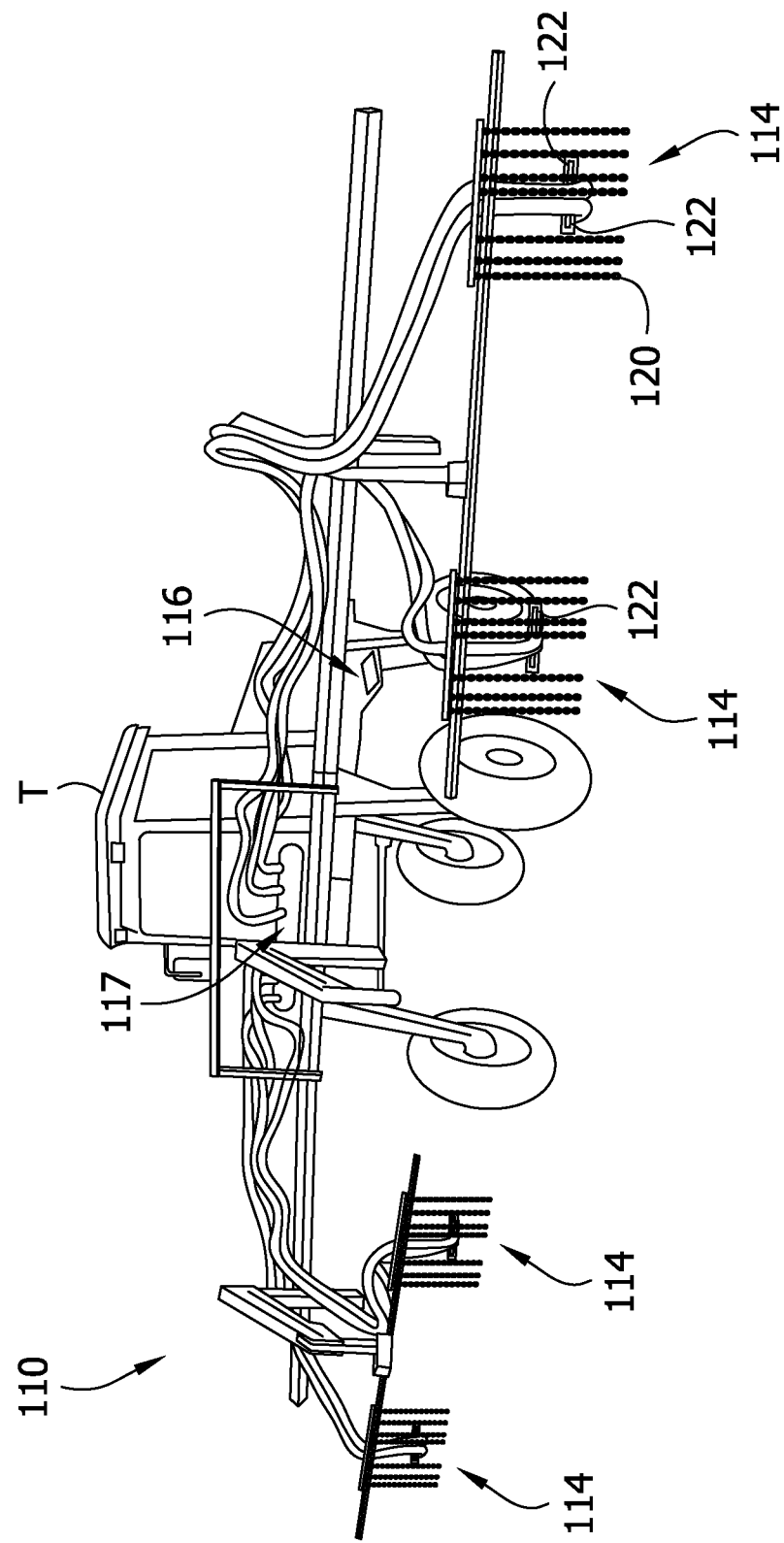

DEVICE AND METHOD FOR POLLINATING PLANTS

FIELD

The present disclosure relates to a device and method for pollinating crop plants and more specifically to a device that blows air from a carriage traveling along rows of crop plants to deliver pollen from pollen-bearing plants to pollen-receiving plants and related methods.

BACKGROUND

Modern agriculture often uses cross-pollinated seeds. To produce cross-pollinated seeds, pollen from one variation of crop plant is used to pollinate crops of another variation of the same plant. The cross-pollinated plants produce a seed crop that can have certain enhanced characteristics in comparison with the two variations from which it was produced. The cross-pollinated seeds are subsequently used to grow grain crops, produce crops, etc. In order for cross-pollinated seeds to be marketable, the grower must ensure that substantially all of the harvested seed was properly obtained from cross-pollinated plants. To ensure the harvested seed is properly cross-pollinated, a grower typically grows the two variations of plants in separate rows in a field. All of the plants of one of the variations are emasculated (i.e., male parts, including the stamen(s), are removed) so that they do not produce any pollen. For example, when cross pollinating corn plants, plants in selected rows are detasseled or topped so that these plants are not capable of pollinating themselves or other corn plants. The emasculated plants may be referred to as pollen-receiving plants because they must receive the pollen from other corn plants in order to be pollinated. The non-emasculated corn plants (i.e., the corn plants with tassels) are pollen-producing or pollen-bearing plants of another variation that pollinate the pollen-receiving plants in order to produce cross-pollinated seed. Pollen from the pollen-bearing plants is delivered to the stigma or female flowers (in the case of corn, silks) to cross-pollinate the pollen-receiving plants.

BRIEF SUMMARY

In one aspect, a pollinating device for pollinating crop plants grown in rows including pollen-bearing rows and pollen-receiving rows comprises a base mountable on a carriage for traveling along the rows of crop plants. At least one pollination unit is mounted on the base for delivering pollen from the crop plants in at least one of the pollen-bearing rows to the crop plants in a plurality of the pollen-receiving rows. Each pollination unit comprises a pollen-releasing apparatus configured to contact male flowers of the crop plants in said at least one of the pollen-bearing rows as the carriage travels along the rows of crop plants and release pollen from the male flowers crop plants in said at least one of the pollen-bearing rows. At least one nozzle adjacent the pollen-releasing apparatus is configured for discharging air along a flow path as the carriage travels along the rows of crop plants such that the discharged air delivers at least some of the released pollen to the pollen-receiving rows of crop plants.

In another aspect, a device for pollinating crop plants grown in rows including pollen-bearing rows and pollen-receiving rows comprises a base mountable on a carriage for traveling in a travel direction oriented parallel to the rows of crop plants. The base has a width and is configured for being mounted on the carriage such that the width is oriented transverse to the travel direction. A pollen blowing system comprises at least one blower configured to provide blown air. Nozzles are mounted on the base at spaced apart positions along the length of the base corresponding with a spacing of the pollen-bearing rows of the rows of crop plants. The nozzles are configured to receive the blown air from the at least one blower and to discharge the blown air toward the crop plants in respective ones of the pollen-bearing rows to deliver pollen from the crop plants in the pollen-bearing rows to the crop plants in the pollen-receiving rows as the carriage travels along the crop plants.

In another aspect, a method of pollinating crop plants grown in rows including pollen-bearing rows and pollen-receiving rows comprises driving a carriage supporting a pollination system along the rows of crop plants. Pollen from the crop plants in the pollen-bearing rows is displaced by contacting a pollen-releasing apparatus of the pollination system with the crop plants in the pollen-bearing rows as the carriage is driven along the rows of crop plants. Air is blown through a nozzle of the pollination system at the displaced pollen to deliver pollen from the crop plants in the pollen-bearing rows to the pollen-receiving rows to pollinate the crop plants in the pollen-receiving rows.

In another aspect, a method of pollinating crop plants grown in rows including pollen-bearing rows and pollen-receiving rows comprises driving a carriage along the rows of crop plants. Air is blown simultaneously through a plurality of spaced apart nozzles supported on the carriage in operative alignment with the crop plants in respective ones of the pollen-bearing rows as the carriage is driven along the rows of crop plants to deliver pollen from the crop plants in the respective ones of the pollen-bearing rows to respective ones of the pollen-receiving rows to pollinate the crop plants in the pollen-receiving rows.

In another aspect, a method of pollinating crop plants grown in rows including pollen-bearing rows and pollen-receiving rows comprises driving a carriage having a forward end and a rearward end along the rows of crop plants in a first forward direction with respect to the rows of crop plants. Air is blown through a nozzle along a flow path oriented in a first transverse direction with respect to the carriage as the carriage is driven in the first forward direction to direct pollen from the crop plants in at least one of the pollen-bearing rows in a pollen delivery direction with respect to the rows of crop plants to deliver the pollen from the at least one of the pollen-bearing rows to a plurality of pollen-receiving rows adjacent to the at least one pf the pollen-bearing rows to pollinate the crop plants in the plurality of adjacent pollen-receiving rows. The carriage is driven in a second forward direction opposite the first forward direction. Air is blown through a nozzle along a flow path oriented in a second transverse direction opposite the first transverse direction with respect to the carriage as the carriage is driven in the second forward direction to direct pollen from the crop plants in at least one other of the pollen-bearing rows in said pollen delivery direction to deliver the pollen from the at least one other of the pollen-bearing rows to another plurality of pollen-receiving rows adjacent to the at least one other of the pollen-bearing rows to pollinate the crop plants in the other plurality of adjacent pollen-receiving rows.

In another aspect, a method of harvesting a crop comprises growing crop plants in a plurality of pollination sets. Each pollination set comprises at least five rows of the crop plants. The crop plants in all but one pollen-bearing row of each pollination set are emasculated. Pollen is delivered from the crop plants in each pollen-bearing row to the emasculated crop plants in the respective pollination set. The crop from the pollination sets is harvested.

Other features will be in part apparent and in part pointed out hereinafter.

BRIEF DESCRIPTION THE DRAWINGS

FIG. 8 is a photograph of another embodiment of a pollination device mounted on a tractor;

Corresponding reference characters indicate corresponding parts throughout the drawings.

DETAILED DESCRIPTION

Figure 1:
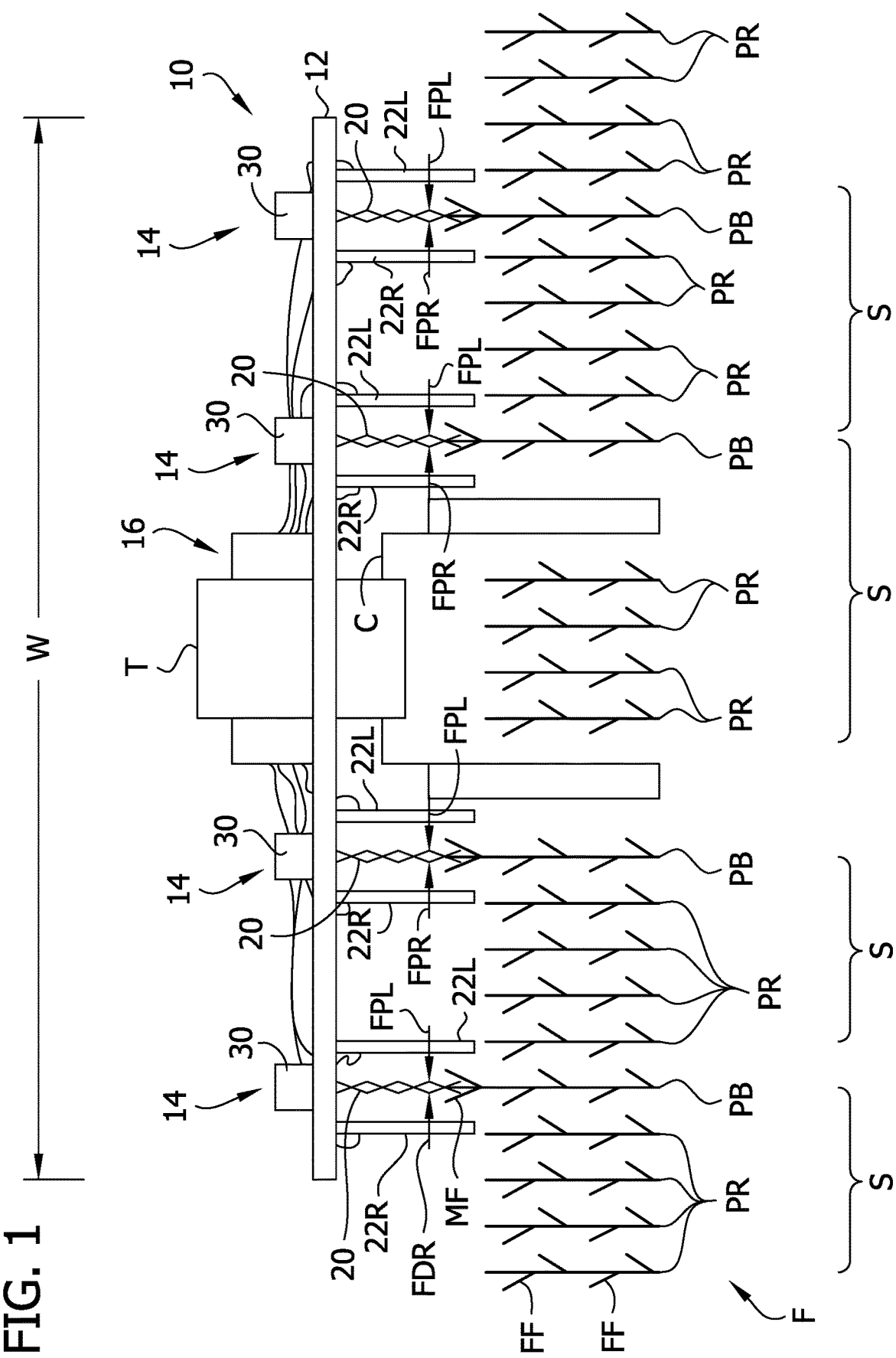
FIG. 1 is a schematic front elevation of a tractor positioned in a corn field and equipped with a pollination device.

Referring to FIG. 1, a field F includes rows of pollen-receiving plants PR and rows of pollen-bearing plants PB. In the illustrated embodiment, the field F is arranged in sets S of five rows, each including one row of pollen-bearing plants PB and four adjacent rows of pollen-receiving plants PR. The plants PB, PR could be planted in other arrangements in other embodiments. The pollen-receiving plants PR have been emasculated (e.g., male flowers are removed) or otherwise modified such that the pollen-receiving plants cannot pollinate themselves or other plants. Emasculation may involve the removal of stamens from bisexual plants in order to avoid self-pollination. Plants can be emasculated mechanically, genetically, or chemically. Even after the pollen receiving plants PR have been emasculated, they include female flowers FF that can be pollinated by the pollen of another plant. In the illustrated field F, the plants PB, PR are corn plants, such as sweet corn or grain corn, and thus the pollen-receiving plants PR have been detasseled and include female flowers FF (i.e., in this case, corn silks). The pollen-bearing plants PB have not been emasculated and grow male flowers MF—in this case, corn tassels—that produce pollen. The pollen-bearing plants PB may also include the female flowers FF—in this case, corn silks. The pollen from the male flowers MF of the pollen-bearing plants PB can be used to pollinate the female flowers FF of the pollen-receiving plants PR, as explained in further detail below. In one or more embodiments, the pollen-bearing plants PB comprise a first variety of a crop plant and the pollen-receiving plants PR comprise a second variety of the same crop plant. Thus, when the pollen-receiving plants PR are pollinated with the pollen of the pollen-bearing plants PB, the pollen-receiving plants produce cross-pollinated seeds that may be used for growing a cross-pollinated variety of the crop plant with certain altered characteristics.

In the illustrated embodiment, a tractor T carries a pollination device, generally indicated at 10, through the field F to pollinate the pollen-receiving plants PR with the pollen from the pollen-bearing plants PB. Although the pollination device 10 is configured to pollinate corn plants PB in the illustrated example, it is understood that in other embodiments a pollination device can be configured to pollinate other crop plants such as, for example, canola; tomato; eggplant; sweet and hot peppers; wheat; amaranth; barley; oat; rye; wild rice; walnut; pecan; brassica such as cabbage, broccoli, spinach; and various types of trees. The tractor T is positioned in the field F to drive along the rows of crop plants PB, PR while supporting the pollination device 10. The tractor T has a forward end and a rearward end and typically travels along the rows of plants PB, PR in the forward direction. In the illustrated embodiment, the tractor T mounts the pollination device 10 adjacent the forward end. As explained in further detail below, the pollination device 10 is used to deliver pollen from the pollen-bearing plants PB to the female flowers FF of the pollen-receiving plants PR. The tractor T comprises a carriage C configured to be driven along the rows of crop plants PB, PR. In the illustrated embodiment, the tractor T comprises a high clearance farm tractor such as an applicator sold by Hagie Manufacturing Company of Clairon, Iowa. Other kinds of tractors or other kinds of vehicles or machines suitable for carrying the pollination device 10 through the field F may be used in other embodiments. For example, manned or unmanned aerial vehicles (e.g., drones), unmanned robots, etc., can be used to carry the pollination device 10 in other embodiments.

In general, the pollination device 10 includes a base 12 and a plurality of pollination units, each generally indicated at 14, which are mounted on the base. As explained in further detail below, each pollination unit 14 is configured to displace or release pollen from at least one row of pollen-bearing plants PB as the tractor T travels through the field F. As further explained below, an air handling system, generally indicated at 16, produces and feeds blown air to each of the pollination units 14, and the pollination units direct the blown air toward the displaced pollen to carry the pollen to respective pollen-receiving plants PR in adjacent rows. Although the illustrated pollination device 10 includes four pollination units 14, in other embodiments the device can include any number of pollination units, including a single pollination unit.

The base 12 of the pollination device 10 has a width W that is oriented transverse (e.g., generally perpendicular) to the forward direction of travel of the tractor T so that the base extends laterally outward from the tractor. The pollination units 14 are mounted on the base 12 at spaced apart positions along the width W of the base. Suitably, the pollination units 14 are spaced apart along the width W of the base 12 at intervals that correspond with the spacing of the rows of pollen-bearing plants PB in the field F so that each pollination unit may be generally aligned with one or more pollen-bearing rows as the tractor T travels through the field F. In the illustrated embodiment, the base 12 comprises a folding farm implement boom. In FIG. 1, the boom 12 is shown in the unfolded or expanded configuration. As is known in the art, the folding boom 12 can also be folded to a compact or folded configuration (not shown) in which the width of the base is narrow enough for the tractor T to drive on a road while supporting the pollination device 10.

Each pollination unit 14 includes a pollen-releasing apparatus 20 supported on the base 12 and positioned to operatively contact the plants PB in at least one of the pollen-bearing rows. The pollen-releasing apparatus is configured to facilitate release of pollen from the pollen-bearing plants PB. Thus, in suitable configurations, each pollen-releasing apparatus 20 is positioned to contact and disturb the male flowers MF (e.g., corn tassels) of the pollen-bearing plants PB to release pollen from the plants. As will be explained in further detail below, the positions of the pollen-releasing apparatus 20 may be adjustable (e.g., automatically adjustable) to account for variation in the height of the male flowers MF of the pollen-bearing plants PB. The illustrated pollen-releasing apparatus 20 each comprises chains that are suspended from the base 12. In one embodiment, each pollen-releasing apparatus 20 comprises a plurality of chains hanging from spaced apart locations along a segment of the width W of the base 12. The pollen-releasing apparatus suitable for facilitating release of pollen from a plant may be of other configurations. For example, in other embodiments, other mechanical pollen-releasing apparatuses such as, for example, one or more rods (not shown) may be used to release pollen from the pollen-bearing plants PB. Such rods may be flexible or rigid. In some embodiments, rods can be configured to move relative to the base of the pollination device (e.g., rods may rotate or spin relative to the base in response to an input from a motor). When a rod is used to form the pollen-releasing apparatus 20, each pollination unit 14 may suitably comprise a vibrator for vibrating the respective rod as it contacts the pollen-bearing plants PB. Other types of pollen-releasing apparatuses may also be used in addition or as an alternative to a mechanical pollen-releasing apparatus such as a rod or a chain. For example, an electrostatic driver for generating an electrostatic force directed at the male flowers MF of the pollen-bearing plants PB may be used in some embodiments. Likewise, a chemical pollen-releasing apparatus for delivering a chemical pollen-releasing agent such as a drying agent or a warming agent may be used to release pollen from the male flowers. Furthermore, an acoustic driver for generating an acoustic signal operative to release pollen from the pollen-bearing plants PB can be used in some embodiments. In still other embodiments, a fluidic pollen-releasing apparatus such as a blower may be used to direct fluid along a flow path extending adjacent the male flowers MF of the pollen-bearing plants PB to release pollen from the male flowers.

Each pollination unit 14 further comprises at least one nozzle 22L, 22R supported on the base 12 in operative alignment with the pollen-releasing apparatus 14 for directing blown air from the air handling system 16 along a respective flow path FPL, FPR to transport the displaced pollen along the flow path. The nozzles 22L, 22R are oriented so that each flow path FPL, FPR extends adjacent the displaced pollen as the tractor T travels along the rows of crop plants PB, PR. More specifically, the nozzles 22L, 22R are spaced apart behind the pollen-releasing apparatus 20 with respect to the forward direction of travel of the tractor T so that the pollen is displaced from the male flowers MF before the air blown along the flow paths FPL, FPR intersects the pollen. Although the illustrated embodiment is configured so that the nozzles 22L, 22R discharge air along flow paths FPL, FPR for carrying pollen that was previously displaced by the pollen-releasing apparatus 20, in other embodiments the pollination units can be configured so that the nozzles discharge air with sufficient force to both displace and deliver the pollen so that no pollen-releasing apparatus is needed.

The air discharged from the nozzle 22L, 22R delivers at least some of the pollen from each row of pollen-bearing plants PB to the pollen-receiving plants PR in the respective pollination set S. In the illustrated embodiment, each pollination unit 14 comprises a left nozzle 22L configured to discharge air along a flow path FPL that extends rightward from the left side of the pollination unit 14 with respect to forward travel of the tractor and a right nozzle 22R configured to discharge air along a flow path FPR that extends leftward (e.g., in a generally opposite direction from the flow path FPL) from a right side of the pollination unit with respect to forward travel of the tractor. (Because FIG. 1 shows a front elevation of the tractor T, the left nozzles 22L are on the right side of each pollination unit 14 in the drawing and the right nozzles 22R are on left side of each pollination unit in the drawing.) As explained in further detail below, the air handling system 16 is configured to selectively deliver blown air to one of the left and right nozzles 22L, 22R in each pollination unit 14 as the tractor travels in the field F along the rows. In the illustrated embodiment, each of the left and right nozzles 22L, 22R comprises an air knife configured to discharge a uniform sheet of laminar airflow along the respective flow path FPL, FPR. In other embodiments, the nozzles may include other types of nozzles, other than air knives, for delivering blown air or other fluid. For example, a single nozzle, multiple nozzles, a fan, or any other mechanism for directing fluid flow may be used in other embodiments. Although each pollination unit 14 includes two nozzles 22L, 22R in the illustrated embodiment, other embodiments can include any suitable number of nozzles, including a single nozzle.

Figure 2:
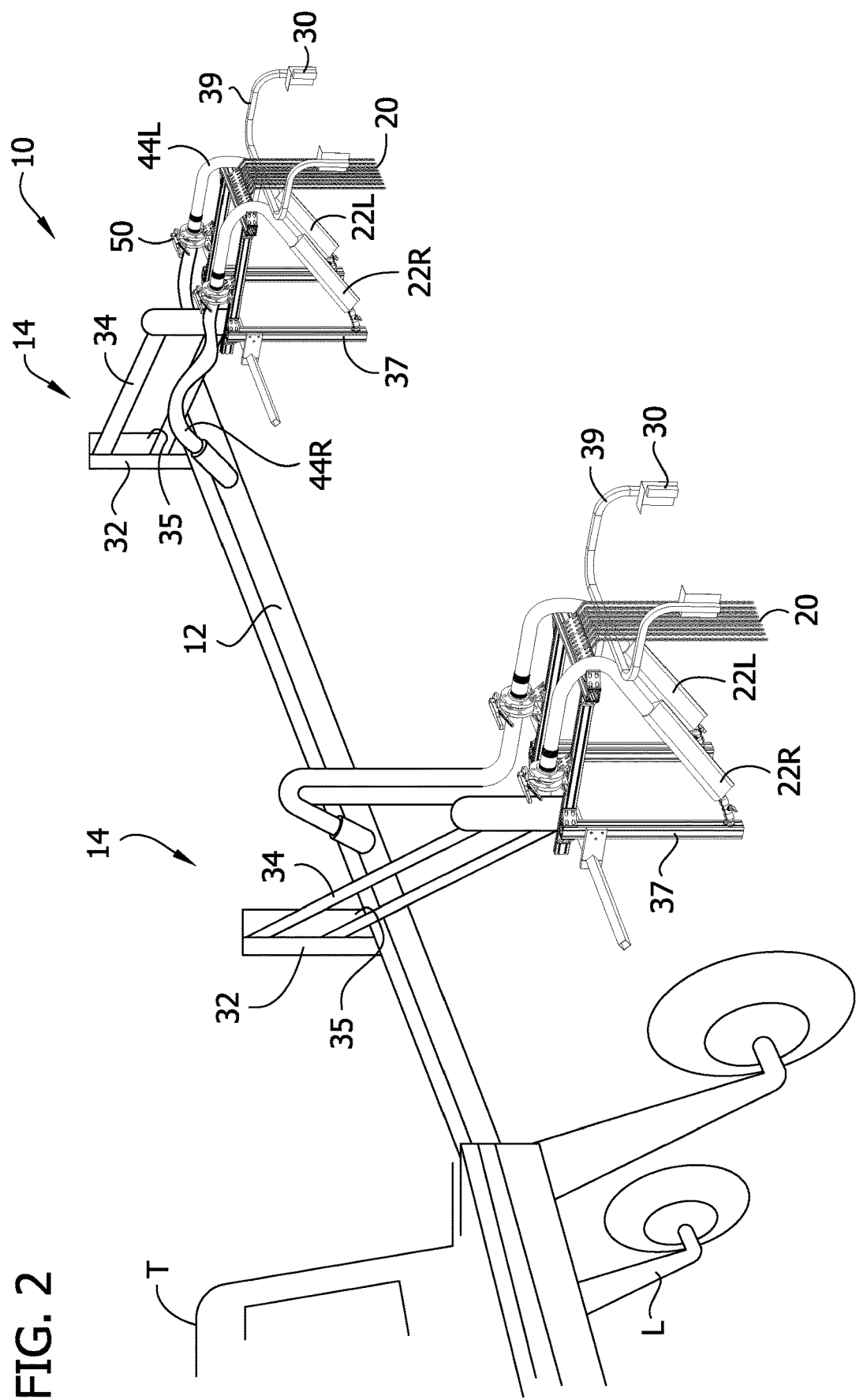
FIG. 2 is a photograph of a portion of the pollination device, illustrating swing arms of two pollination units thereof in different positions.

Each pollination unit 14 is configured for selectively adjusting the positions of the pollen-releasing apparatus 20 and the left and right nozzles 22L, 22R in order to optimize delivery of the pollen from the pollen-bearing plants PB to the respective pollen-receiving plants PR. Referring to FIGS. 1 and 2, each pollination unit 14 comprises a crop height sensor 30 and a lift 32 for adjusting the height of the pollination unit for operative heightwise alignment with the male flowers MF of the pollen-bearing plants PB in a particular field F. As is known in the art, the crop height sensor 30 is configured to detect the height of the tops of the crop plants PB, PR as the tractor T travels across the field. The lift 32 comprises a swing arm 34 that is pivotably mounted on the base 12. A hydraulic driver 35 (e.g., a piston) driven by the hydraulic drive system of the tractor T is operatively connected to the swing arm 34 and the base 12 for pivotably adjusting the position of the swing arm with respect to the base. A chassis 37 is secured to the free end of the swing arm 34 for mounting the pollen-releasing chains 20 and the nozzles 22L, 22R on the swing arm, and a sensor mounting bracket 39 separately mounts the crop height sensor 30 to the swing arm. As explained below, one of the chassis 37 and the sensor mounting brackets 39 can be adjustable to adjust the relative positions of the crop height sensor 30 and the pollen-releasing chains 20 and the nozzles 22L, 22R.

Figure 11:
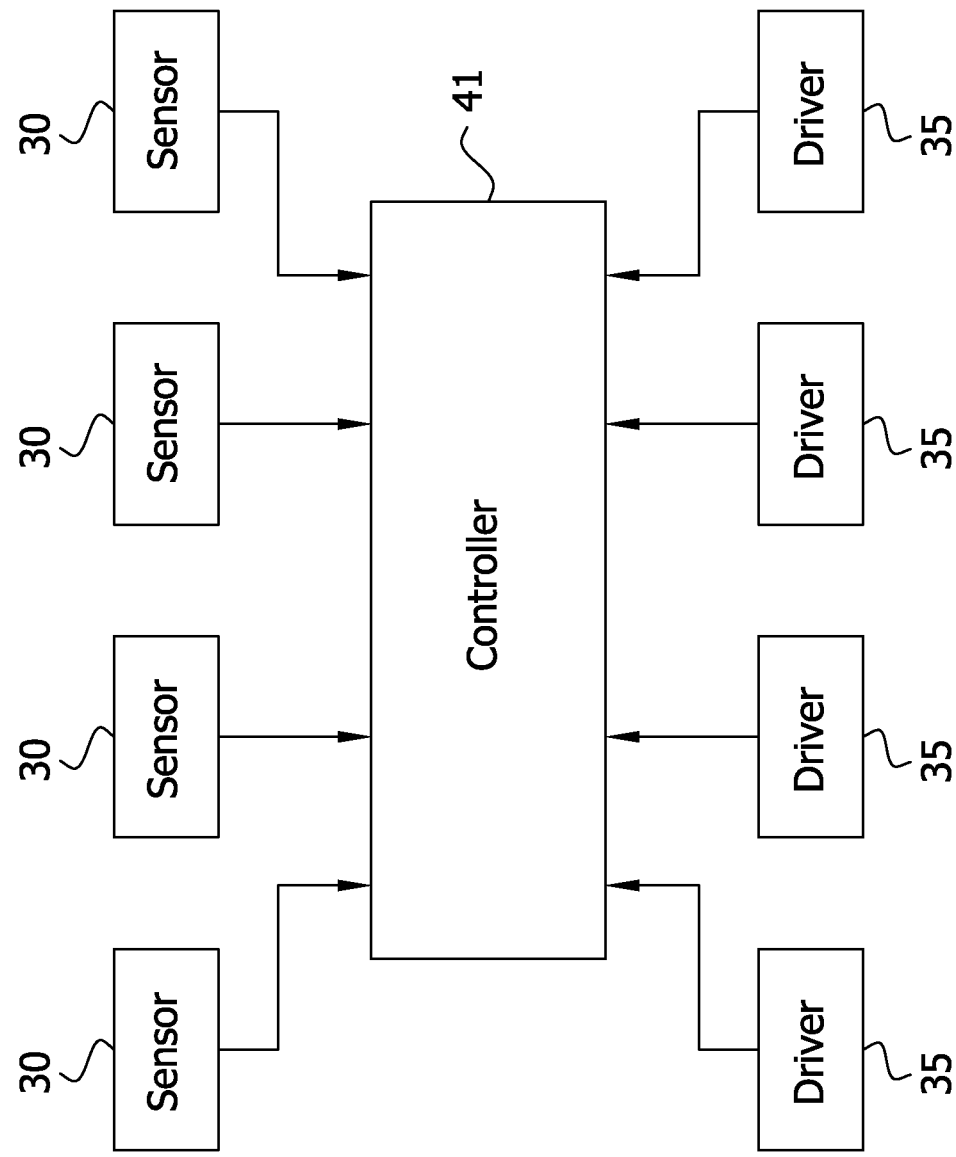
FIG. 11 is a schematic illustration of a control system of the pollination device.

Referring to FIG. 11, in the illustrated embodiment, the pollination device 10 is configured to automate the heightwise adjustment of each of the pollination units 14. In use, each crop height sensor 30 transmits a crop height signal representative of a sensed height of the plants PB in the aligned pollen-bearing row to a controller 41. The controller 41 uses the crop height signals to generate a height adjustment signal for each of the respective pollination units 14. The controller 41 transmits the height adjustment signal to the hydraulic driver 35. And in response to receiving the crop height adjustment signal, the driver 35 drives pivoting movement of the swing arm 34 to adjust the height of the pollination unit 14 so that the pollen-releasing apparatus 20 is aligned along the heights of the plants PB, PR with the male flowers MF of the pollen-bearing plants. Although the illustrated embodiment, uses a single controller 41 to control all of the lifts 32, it is understood that other numbers of controllers (e.g., one for each lift, etc.) can be used in other embodiments. Though the illustrated embodiment automatically adjusts the height of the pollination units 14, in other embodiments the lifts can instead be adjusted by manually pivoting the swing arm 34 to the desired height before pollinating the field F or using an operator controlled actuator in the cab of the tractor T.

Figure 3:
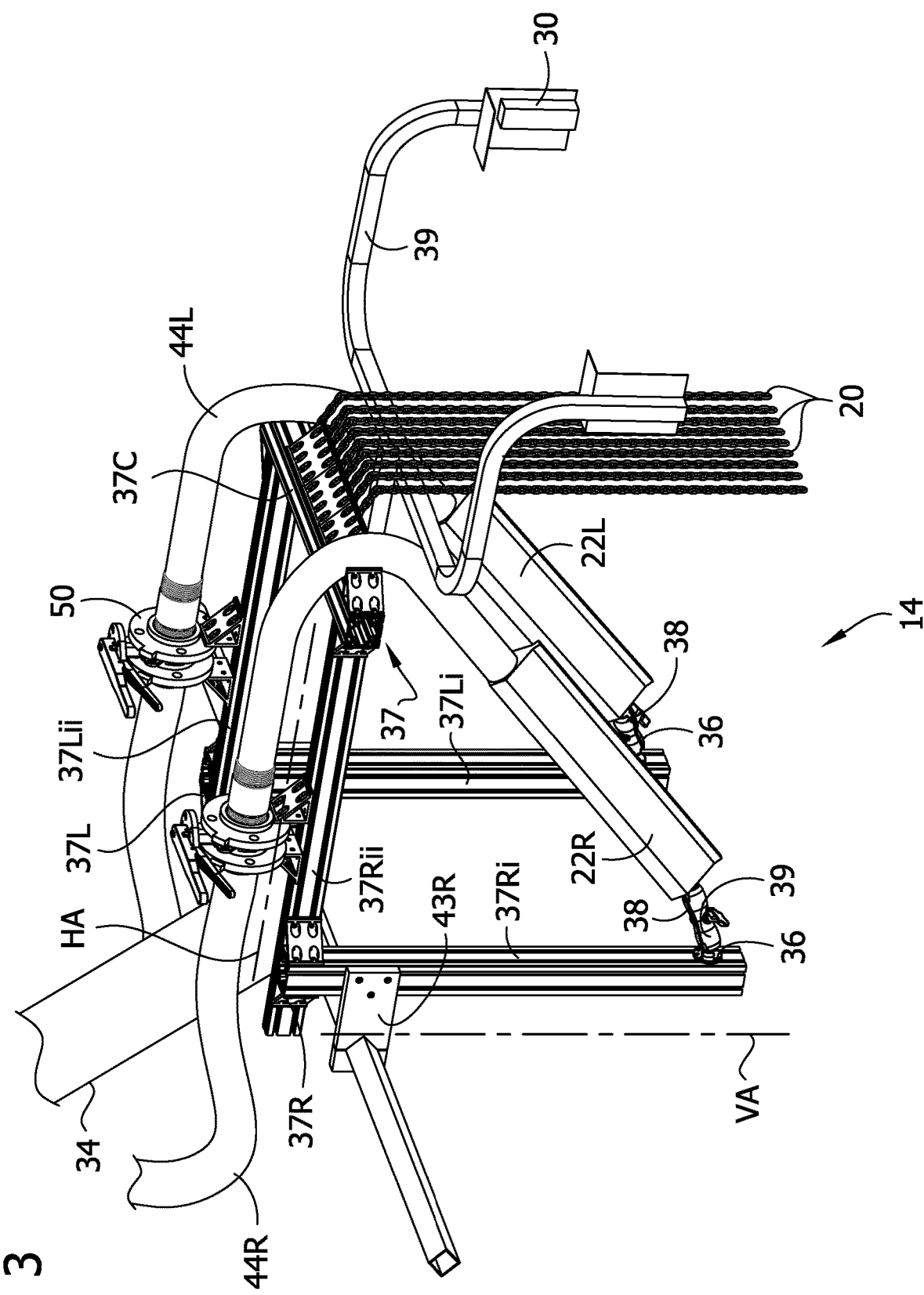
FIG. 3 is a photograph of one pollination unit.

Referring to FIG. 3, the chassis 37 is configured to support the pollen displacement chains 20 and the nozzles 22L, 22R on the swing arm 34. The illustrated chassis 37 comprises a left frame assembly 37L, a right frame assembly 37R, and a crossbar 37C connecting the left frame assembly and the right frame assembly. As explained in further detail below, the left nozzle 22L is movably mounted on the left frame assembly 37L and the right nozzle 22R is movably mounted on the right frame assembly. The pollen-releasing chains 20 are fixed to the cross bar 37C and suspended from spaced apart locations along the length of the crossbar. Each frame assembly 37L, 37R includes a vertical frame member 37Li, 37Ri and a horizontal frame member 37Lii, 37Rii. Opposite ends of the cross bar 37C are fixedly attached to the forward ends of the horizontal frame members 37Lii, 37Rii.

Left and right swing arm mounts 43L, 43R are attached to the swing arm 34 and are selectively fastenable to the respective vertical frame members 37Li, 37Ri to secure the chassis 37 to the swing arm. In the illustrated embodiment, the vertical frame members 37Li, 37Ri define vertically extending tracks that facilitate sliding the vertical frame members with respect to the mounts 43L, 43R along the lengths of the tracks to respectively adjust the positions of each of the left and right frame assemblies 37L, 37R with respect to the swing arm 34 along a vertical axis VA. Thus, by adjusting the positions of the left and right frame assemblies 37L, 37R along the vertical axis VA, the heights of the nozzles 22L, 22R and the pollen-releasing chains 20 in relation to the swing arm 34 can be adjusted. Since the crop height sensor 30 is mounted on the swing arm by a separate bracket 39, adjusting the positions of the left and right frame assemblies 37L, 37R along the vertical axis VA likewise adjusts the positions of the chassis 37, the nozzles 22L, 22R, and the chains 20 with respect to the crop height sensor 30. In one or more embodiments, each pollination unit 14 comprises actuators (not shown) operatively connected to the controller 41 for adjusting the positions of the left and right frame assemblies 37L, 37R along the vertical axis VA automatically or in response to operator inputs. But in the illustrated embodiment, the heights of the frame assemblies 37L, 37R are manually adjustable by loosening bolts securing the vertical frame members 37Li, 37Ri to the swing arm mounts 43L, 43R, slidingly adjusting the position of the frame assemblies along the vertical axis VA, and tightening the bolts to secure the chassis 37 in the desired position.

In the illustrated embodiment, the horizontal frame members 37Lii, 37Rii define horizontally extending tracks that facilitate sliding the horizontal frame members 37Li, 37Ri along the lengths of the tracks to respectively adjust the positions of the horizontal frame members and the crossbar 37C with respect to the swing arm 34 and the vertical frame members along a horizontal axis HA. By adjusting the positions of the crossbar 37C, the spacing between the pollen-releasing chains 20 and the swing arm 34 can be adjusted. As explained below, the nozzles 22R, 22L are movably mounted on the vertical frame members 37Li, 37Ri and not the horizontal frame members 37Lii, 37Rii or the cross bar 37C. Thus, movement of the crossbar 37C with respect to the vertical frame members 37Li, 37Lii along the horizontal axis HA adjusts the distances between the pollen-releasing chains 20 and the nozzles 22L, 22R. Since the crop height sensor 30 is mounted on the swing arm by a bracket 39 separate from the chassis 37, adjusting the positions of the cross bar 37C along the horizontal axis HA also adjusts the distance between the chains 20 and the crop height sensor 30 along the horizontal axis. In one or more embodiments, each pollination unit 14 comprises actuators (not shown) operatively connected to the controller 41 for adjusting the positions of the left and right horizontal frame members 37Lii, 37Rii along the horizontal axis HA automatically or in response to operator inputs. But in the illustrated embodiment, the positions of the frame members 37Lii, 37Rii and the cross bar 37C are manually adjustable by loosening bolts securing the horizontal frame members to the vertical frame members 37Li, 37Ri, slidingly adjusting the position of the horizontal frame members along the horizontal axis HA, and tightening the bolts to secure the chassis 37 in the desired position.

The illustrated pollination device 10 is further configured for selectively adjusting the orientation of the individual nozzles 22L, 22R to optimize the orientation of the flow paths FPL, FPR for maximizing pollen delivery. Referring to FIG. 3, an adjustable mount 36 mounts each nozzle 22L, 22R to a mounting bracket of the swing arm 34. The munt 36 is attached to one end of the respective nozzle 22L, 22R and slidably received in tracks of the respective vertical frame member 37Li, 37Ri. The mount 36 is slidable with respect to the respective vertical frame member 37Li, 37Ri along the vertical axis VA to adjust the position of the respective nozzle 22L, 22R. In one or more embodiments, each pollination unit 14 comprises actuators (not shown) operatively connected to the controller 41 adjusting the positions of the mounts 36 along the vertical axis VA automatically or in response to operator inputs. But in the illustrated embodiment, the positions of the mounts 36 are manually adjustable by loosening bolts securing the mounts to the vertical frame members 37Li, 37Ri, slidingly adjusting the position of the mounts along the vertical axis VA, and tightening the bolts to secure the nozzles 22L, 22R in the desired position. In the illustrated embodiment, one mount 36 mounting a single respective nozzle 22L, 22R is slidably mounted on a front side of each vertical frame member. However, in other embodiments, more than one mount 36 can be mounted on the vertical frame member (e.g., another mount could be slidably mounted in a rear side of each vertical frame member, etc.) to mount more than one nozzle on one or both sides of the chassis.

In the illustrated embodiment, each mount 36 includes first and second ball joints 38, 39 that allow the orientations of the nozzles 22L, 22R to be adjusted with respect to the chassis 37. The second ball joint 39 is configured for selective movement with respect to the first ball joint 38 in two planes, and each nozzle 22L, 22R is configured for selective movement with respect to the second ball joint in two planes. Accordingly, the double ball joint mount 36 allows the orientation of the nozzle 22L, 22R to be selected from a wide range of orientations. Adjusting the orientation of the nozzle 22L, 22R using the mounts 36 adjusts the orientation of the nozzles with respect to the chassis 37, the pollen-releasing chains 20, the crop height sensor 30, etc. The orientations of the nozzles 22L, 22R are suitably selected so that, as the tractor T travels along the rows in the field F and the pollen-releasing chains 20 release pollen from the pollen-bearing plants PB, the air discharged from the nozzles transports the displaced pollen toward the female flowers FF of the pollen-receiving plants PR in the corresponding pollination set S. When the nozzles 22L, 22R are in the desired orientations, a lock down knob can be tightened to fasten the mounts 36 in position to maintain the orientations of the nozzles in use. In one or more embodiments, each pollination unit 14 comprises actuators (not shown) operatively connected to the controller 41 for adjusting the orientations of the nozzles 22L, 22R using the double ball joint mounts 36 automatically or in response to operator inputs. But in the illustrated embodiment, the mounts 36 are configured for manually adjusting the orientations of the nozzles 22L, 22R.

Figure 4:
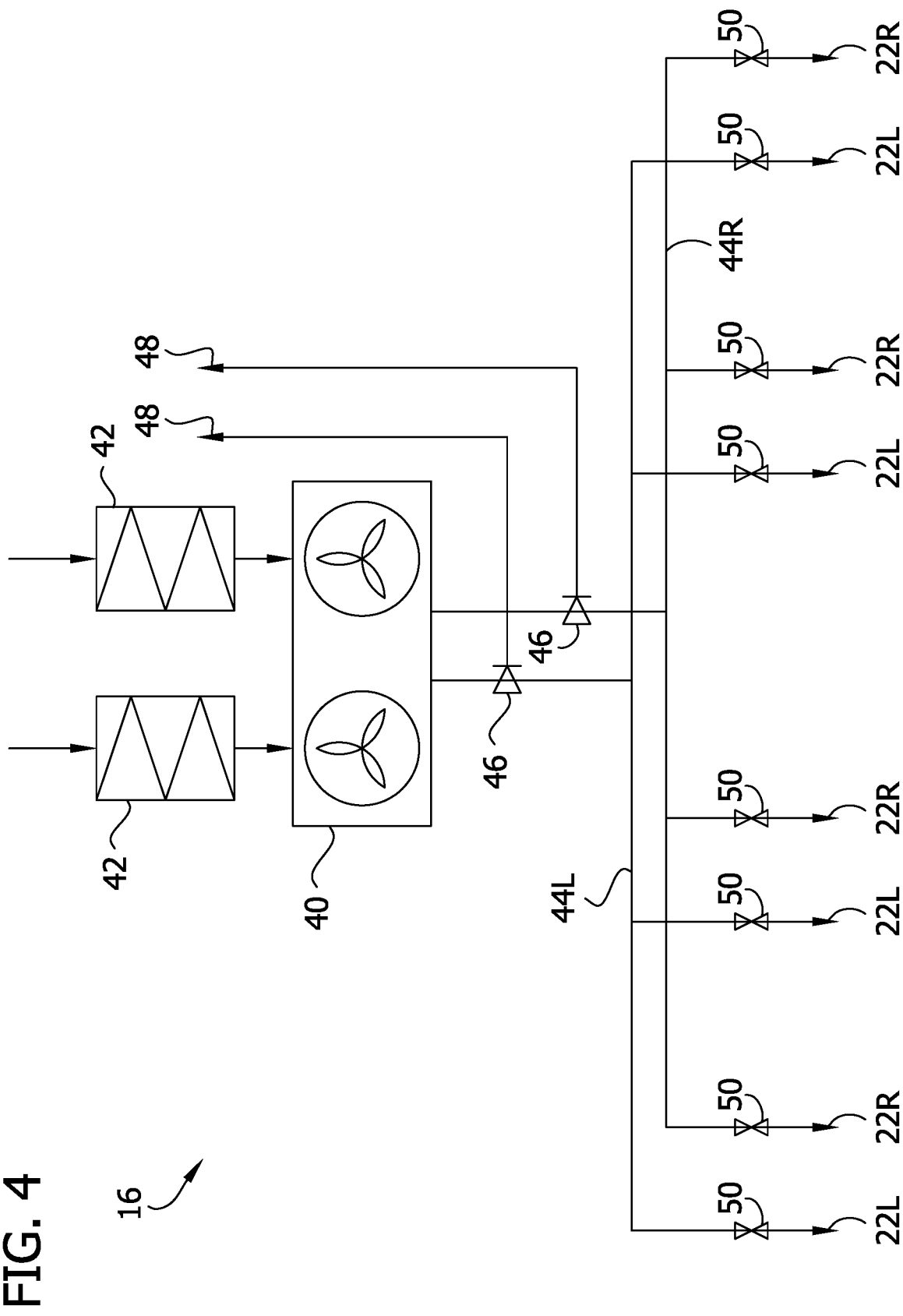
FIG. 4 is a schematic diagram of an air handling system of the pollination device.
Figure 5:
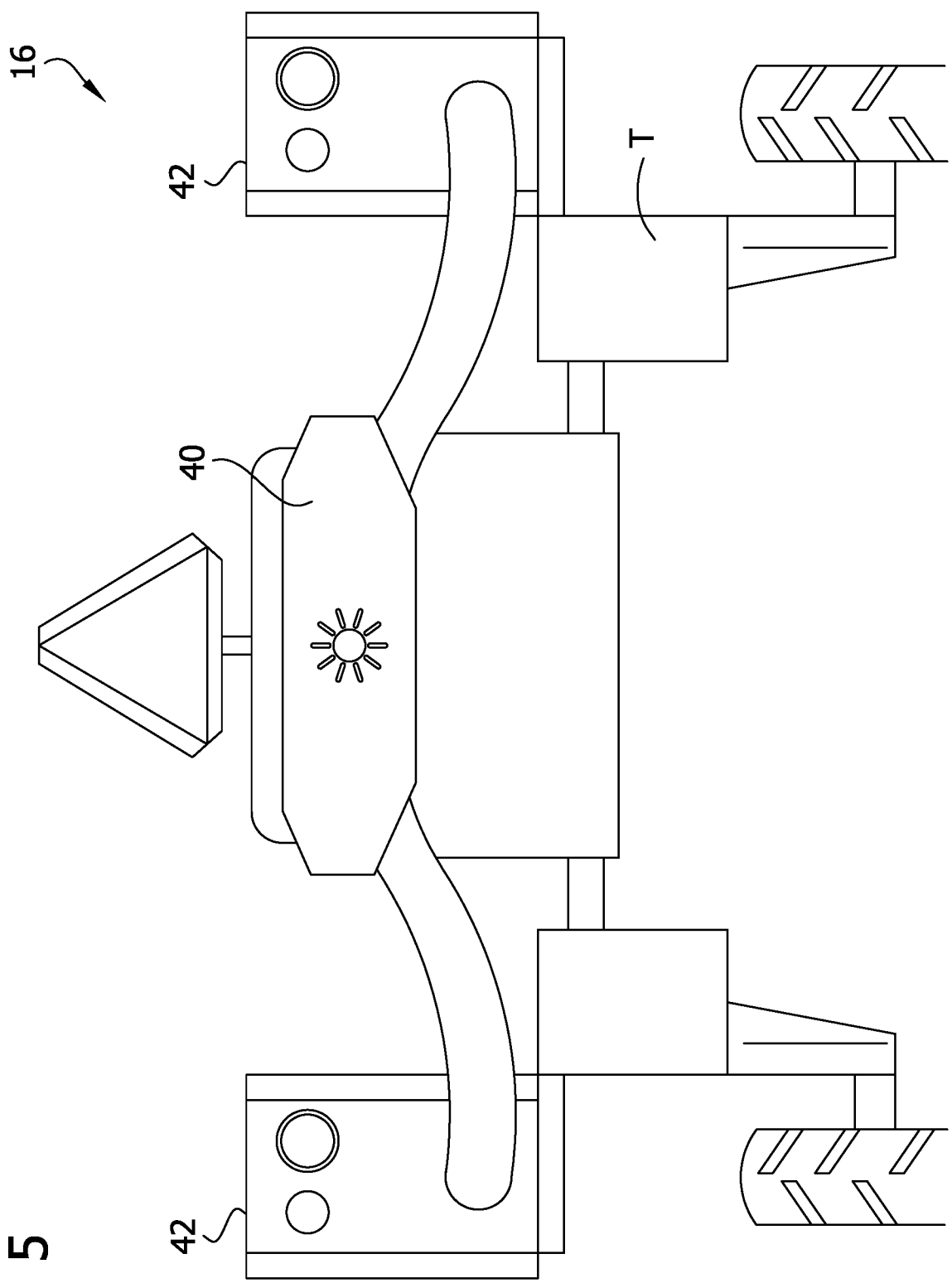
FIG. 5 is a photograph an intake and a blower of the air handling system mounted on the tractor.
Figure 6:
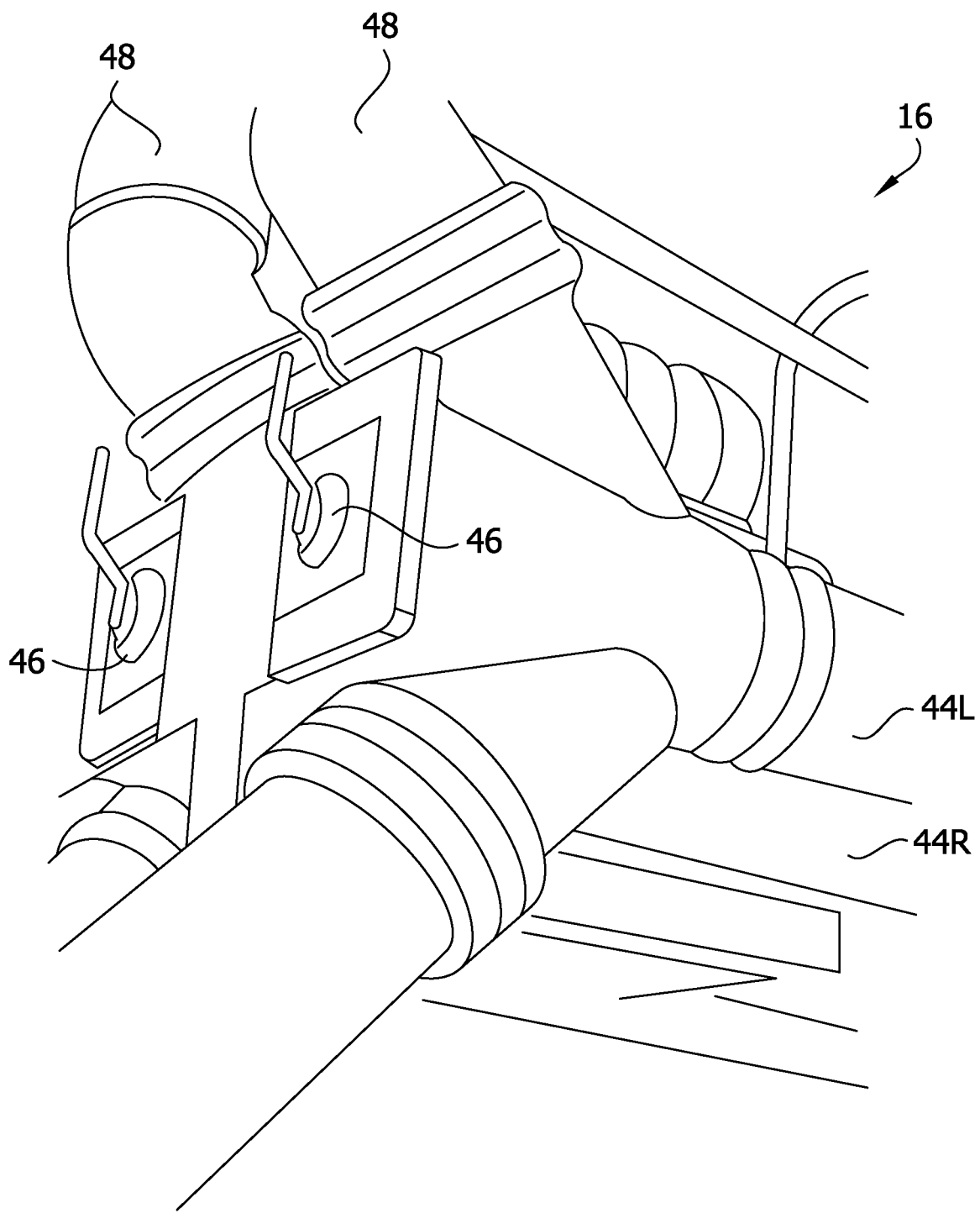
FIG. 6 is a photograph of two ventilation valves of the air handling system.

Referring to FIGS. 4-6, the air handling system 16 is mounted on the tractor T for supplying blown air to the nozzles 22L, 22R of each of the pollination units 14. The air handling system 16 generally comprises a blower 40 and air handling conduit networks 44L, 44R for conveying blown air from the blower to the nozzles 22L, 22R. In the illustrated embodiment, the blower 40 comprises a dual fan blower that is driven by the hydraulic drive system of the tractor T, but other embodiments can use other types of blowers without departing from the scope of the invention. In one or more embodiments, the blower 40 is configured to provide the blown air to the nozzles 22L, 22R such that the air discharged from the nozzles exits at least at about 30 miles per hour. The air exiting the nozzles may be of other speeds. In addition, the speed of the discharged air may be selectively adjustable during operation, such as by controlling an actuator in the cab of the tractor T (or by automatic control of an actuator using the controller 41). The illustrated blower 40 is configured to draw in ambient air through intake filters 42. Because the pollination device 10 functions by blowing pollen through the ambient environment, it is possible for a blower 40 to draw in displaced pollen if the filters 42 are not used. Residual pollen in the air handling system 16 from one field F can contaminate cross-pollination efforts in another field, and thus the filters 42 are suitably configured to filter out pollen from the ambient air so that it does not contaminate the air handling system 16.

The illustrated air handling system 16 comprises left and right conduit networks 44L, 44F for separately delivering blown air from the blower 40 to the left nozzles 22L and the right nozzles 22R. Each conduit network 44L, 44R includes a ventilation valve 46 for selectively diverting the blown air to a vent 48 of the respective conduit network. In an open position, the ventilation valve 46 directs the blown air to the respective nozzles 22L, 22R, and in a closed position the ventilation valve disconnects the blown air from the nozzles and instead delivers the blown air to the respective vent 48. Thus, by alternating which of the two ventilation valves 46 is open, blown air can be selectively provided to either the left nozzles 22L or the right nozzles 22R. As explained in further detail below, selectively alternating between the left nozzles 22L and the right nozzles 22R can be used to efficiently pollinate the field F. In certain embodiments, the ventilation valves 46 are controlled electronically using an actuator accessible to the operator from the cab of the tractor T. In other embodiments, the ventilation valves 48 are manually activated. In still other embodiments, control of the ventilation valves 46 is automated using the controller 41.

In the illustrated embodiment, an air balance valve 50 is fluidly coupled to the conduit network 44L, 44R between each nozzle 22L, 22R and the blower 40. The air balancing valves 50 are configured to be incrementally opened and closed to individually adjust the amount of air flow to each nozzle 22L, 22R. In one or more embodiments, the air balance valves 50 comprise manually adjustable butterfly valves, but other types of valves may also be used in other embodiments (e.g., electronically actuated valves controlled by an actuator in the cab of the tractor T or the controller 41). As can be seen in FIG. 1, the conduit networks 44L, 44R span a greater distance to reach the outboard nozzles 22L, 22R than the inboard nozzles. As a result, air flow losses occur in the conduit networks 44L, 44R between the inboard nozzles 22L, 22R and the outboard nozzles. However, it may be preferable for the air discharged from the outboard nozzles 22L, 22R to exit at the same speed as the inboard nozzles 22L, 22R so that pollen is distributed from each pollination unit 14 consistently. The air balance valves 50 permit slight adjustments to be made to the amount of blown air that is supplied to each nozzle 22L, 22R to balance the air flow amount from each nozzle in a way that accounts for losses through the conduit networks 44L, 44R.

Referring again to FIG. 1, a suitable method of using the pollination device to grow and harvest crop plants will now be briefly described. The method described below is specifically directed toward the harvest of cross-pollinated corn seed. However, the same techniques can be employed in the growing and harvesting of other types of crops. Initially two variations of corn seed are planted in pollination sets S that are configured for being pollinated using the pollination device 10. As explained above, the illustrated pollination device 10 includes pollination units 14 that are spaced apart along the width of the base 12 to pollinate respective sets S including four rows of a pollen-receiving variety of corn PR spaced apart from one side of a single row of a pollen-bearing variety of corn PB. Thus, the method initially comprises growing a plurality of sets S of corn plants PB, PR, each comprising five rows, including one pollen-bearing row and four adjacent pollen-receiving rows. In other embodiments, the method can comprise growing pollination sets comprising other numbers of rows of plants (e.g., less than five rows in each set or greater than five rows in each set, such as at least six rows, at least seven rows, at least eight rows, at least nine rows, at least ten rows, at least eleven rows, at least twelve rows, etc.; pollination sets S may also include more than one row or pollen-bearing plants PB in each set). Although, each pollination set S includes only one row of pollen-bearing plants PB in the illustrated embodiment, in other embodiments more than one pollen-bearing row can be included in each set.

In one example, after planting the seed, the corn plants PB, PR are grown until the pollen-receiving plants reach a suitable level of maturity for detasseling. At this point, the pollen-receiving plants PR are detasseled so the pollen-bearing plants PB are substantially the only source of pollen for the field F. After detasseling or otherwise emasculating the pollen-receiving plants PR, all of the plants in the field are grown until the pollen-bearing plants PB bear pollen suitable for pollination. The pollen-receiving plants PR could also be emasculated (i.e., made incapable of pollenizing itself and other pollen-receiving plants) in other ways. For example, in certain embodiments, the pollen-receiving plants PR are emasculated genetically, by imparting cytoplasmic male sterility. In other embodiments, Roundup Hybridization System is used to emasculate the pollen-receiving plants PR.

After the plants PB, PR are ready for pollination, an operator installs the pollination device 10 on the tractor T and arranges the pollination units 14 for pollinating the plants. The operator may, for example, measure or visually inspect the heights of the pollen-bearing plants PB and adjust the height of the swing arm 34 so that the pollen displacement chains 20 are arranged for contacting the tassels MF. In addition, the operator may measure or visually inspect the heights of the pollen-receiving plants PR and measure or otherwise determine ambient wind conditions and adjust the positions of the air nozzles 22L, 22R to orient the flow paths FPL, FPR to optimally distribute the displaced pollen to the pollen-receiving plants. Alternatively, the heights of the pollination units 14 may be automatically adjusted through use of the sensors, controller, and the actuators (e.g., hydraulic pistons), as explained above. Moreover, the positions of the air nozzles 22L, 22R on the pollination units may be automatically adjusted to account for wind speeds, wind directions, and/or other data detected by sensors in communication with the controller.

Figure 7:
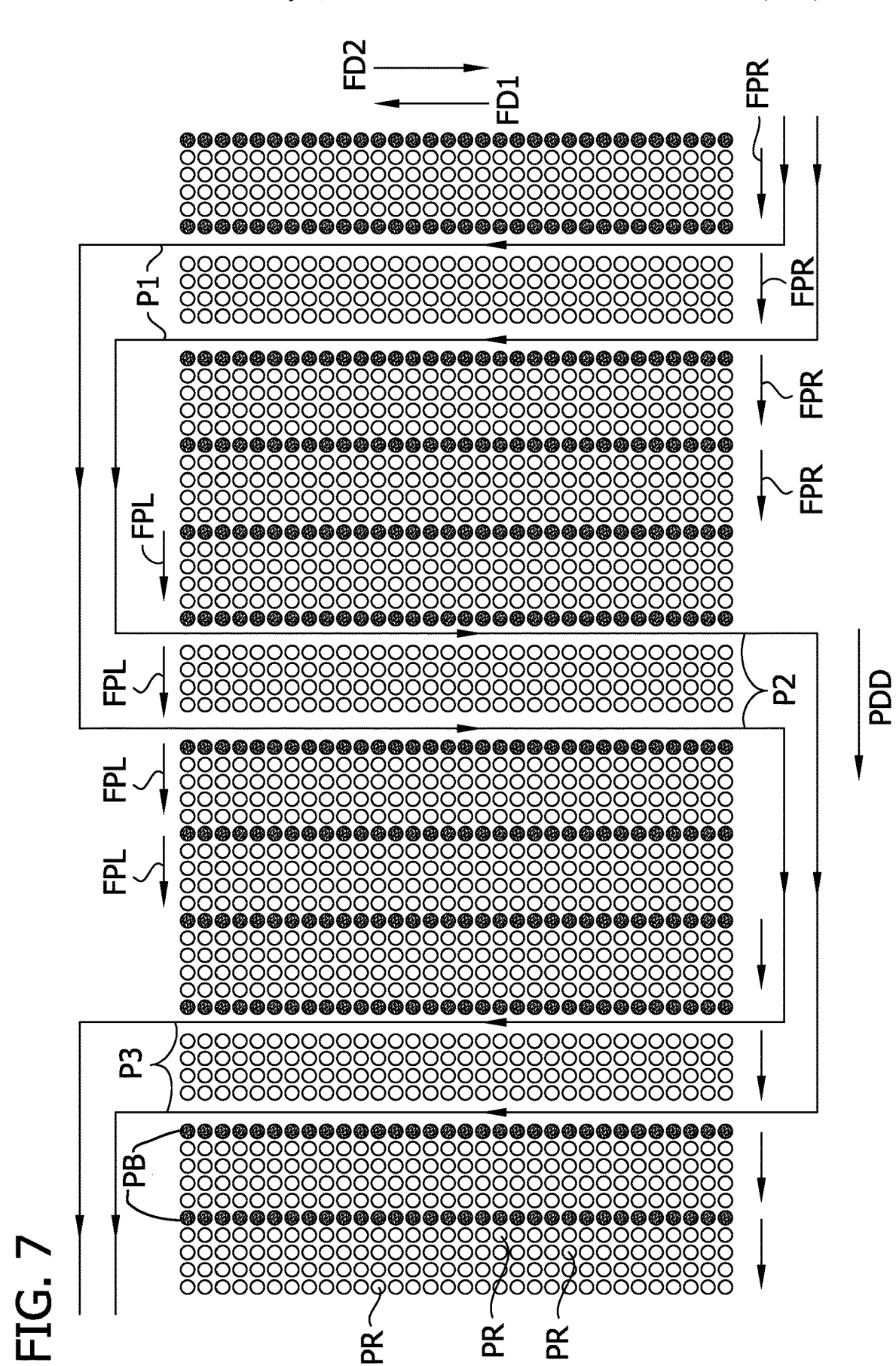
FIG. 7 is a diagram of a travel path along which the tractor travels through a field and pollination paths along which the pollination device delivers pollen as it is carried by the tractor.

Referring to FIG. 7, in the illustrated embodiment, the tractor T is driven through the field F of corn plants PB, PR along a serpentine path extending along a plurality of segments P1-P3. The operator initially switches the ventilation valve 46 for the right conduit network 44R to the open position and switches the ventilation switch for the left conduit network 44L to the closed position. With the pollination device 10 configured so that air is being blown through the right nozzles 22R but not the left nozzles 22L, the operator drives the tractor T and the pollination device 10 in a first forward direction FD1 along a first path segment P1. As the tractor T is driven along the first path segment P1, the pollen displacement chains 20 displace pollen from the rows of pollen-bearing plants PB with which they are aligned. And as the pollen is displaced, the right nozzles 22R blow air along the flow paths FPR, which are oriented in a leftward direction with respect to the first forward direction FD1 of the tractor T. Accordingly, each pollination unit 14 blows pollen in a pollen delivery direction PDD that extends leftward with respect to the field F as shown in FIG. 7. The pollen from each row of pollen-bearing plants PB is therefore delivered to the four adjacent rows of pollen-receiving plants PR to the left of the respective pollen-bearing row.

After the tractor T has traveled along the first path segment P1 through the first sets S of rows, it turns toward a second segment P2. Before driving the tractor T along the second segment P2, the operator switches the ventilation valve 46 for the right conduit network 44R to the closed position and switches the ventilation switch for the left conduit network 44L to the open position. The pollination device 10 thus blows air through only the left nozzles 22L and not the right nozzles 22R. The operator then drives the tractor T and the pollination device 10 in a second forward direction FD2, opposite the first forward direction FD1, along the second path segment P2. As the tractor T is driven along the second path segment P2, the pollen displacement chains 20 displace pollen from the rows of pollen-bearing plants PB with which they are aligned. And as the pollen is displaced, the left nozzles 22L blow air along the flow path FPL, which is oriented in a rightward direction with respect to the tractor T, and a leftward direction with respect to the field F as shown in FIG. 7. Accordingly, each pollination unit 14 blows pollen in the same pollen delivery direction PDD along both the first path segment P1 and the second path segment P2.

The steps of switching the ventilation valves 46 and driving the tractor T along subsequent path segments are repeated until all of the sets S in the field F are pollinated. It can be seen that using pollination units 14 with an arrangement of switchable, opposing nozzles 22L, 22R enables the pollination device 10 to distribute pollen in the same pollination direction PDD while driving back and forth in a serpentine pattern across a field F. This ensures that the pollen is distributed in a relatively uniform manner throughout the field F because the pollen is carried in substantially the same direction with substantially the same force during each pass of the tractor T through the field. Wind and other environmental factors that are generally consistent during pollination would have substantially equivalent effects on the distribution of pollen in each of the pollination sets S.

Figure 10:
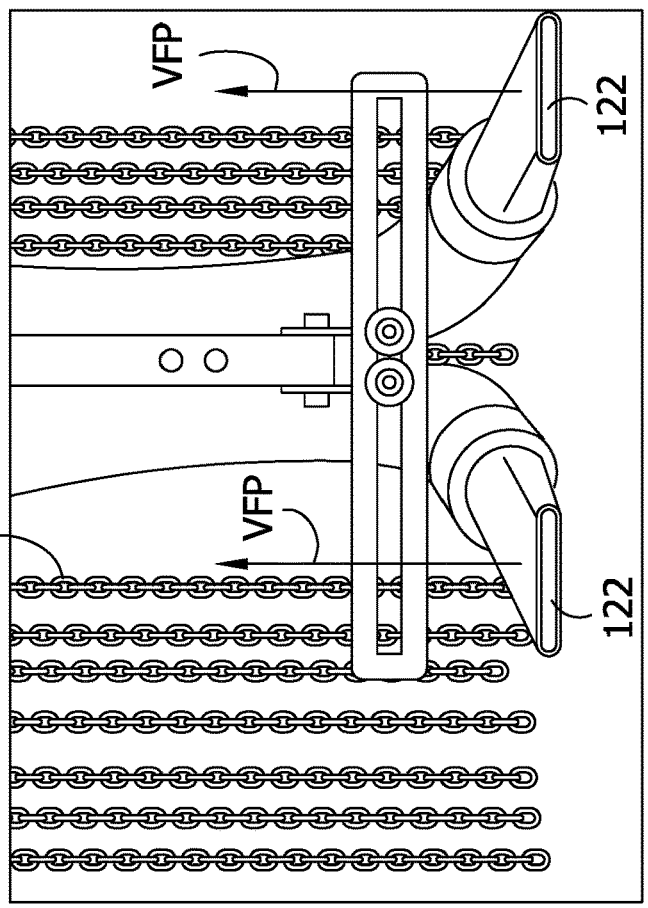
FIG. 10 is a photograph of a pollination unit of the pollination device of FIG. 8.
Figure 9:
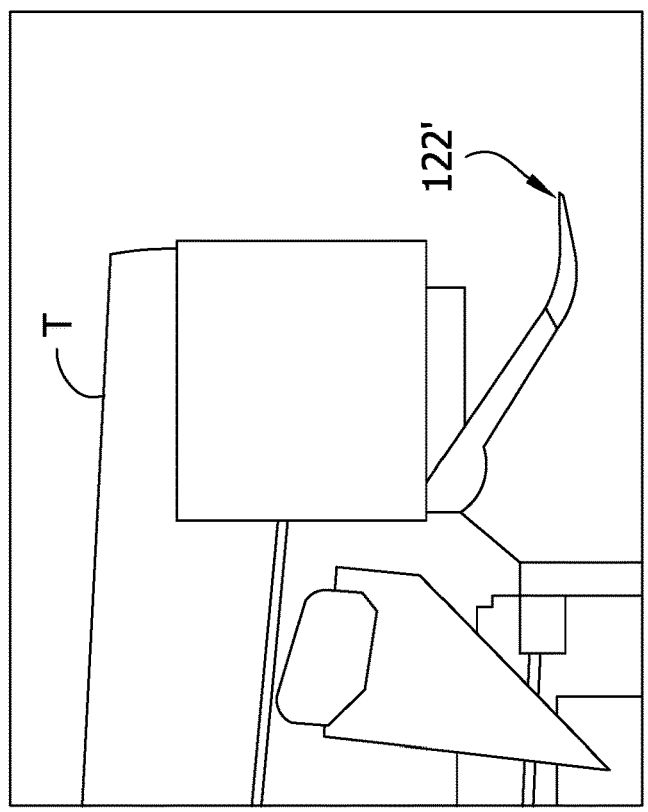
FIG. 9 is a photograph of a rear nozzle of the pollination device of FIG. 8.

Referring to FIGS. 8-10 another embodiment of a pollination device mounted on the tractor T is generally indicated at reference number 110. The pollination device 110 is substantially similar to the pollination device 10 and, like the pollination device 10, includes a plurality of pollination units 114 mounted on a base 112 at spaced apart positions along the width of the base. Each pollination unit 114 includes a pollen-releasing apparatus 120, such as pollen-releasing chains, etc., and first and second nozzles 122 that are operatively connected to an air handling system 116. A blower (not shown) forces air through a distributor 117 and conduits of the air handling system 116 to each of the nozzles 122. Unlike the pollination units 14, the nozzles 122 of the pollination units 114 are not oriented in opposing directions. Rather, the nozzles 122 point upwardly to blow air along a vertically oriented flow path VFP, as shown in FIG. 10. Thus, as the tractor T travels along the rows of plants PB, PR and the pollen-releasing apparatus 120 displaces pollen from the male flowers MF, the nozzles 122 discharge air along the vertical flow path VFP to direct the displaced pollen upward above the plants. Eventually, the blown pollen falls down to pollinate the plants PB, PR in a manner that simulates natural pollination processes. Referring to FIG. 9, the tractor T is equipped with a further nozzle 122' at its rear end, which continues to force the pollen upward as the tractor passes. Because the movement of pollen using the pollination device 110 is less directional than with the pollination device 10, the need for switching between nozzles with each field pass is eliminated.

Figure 12:
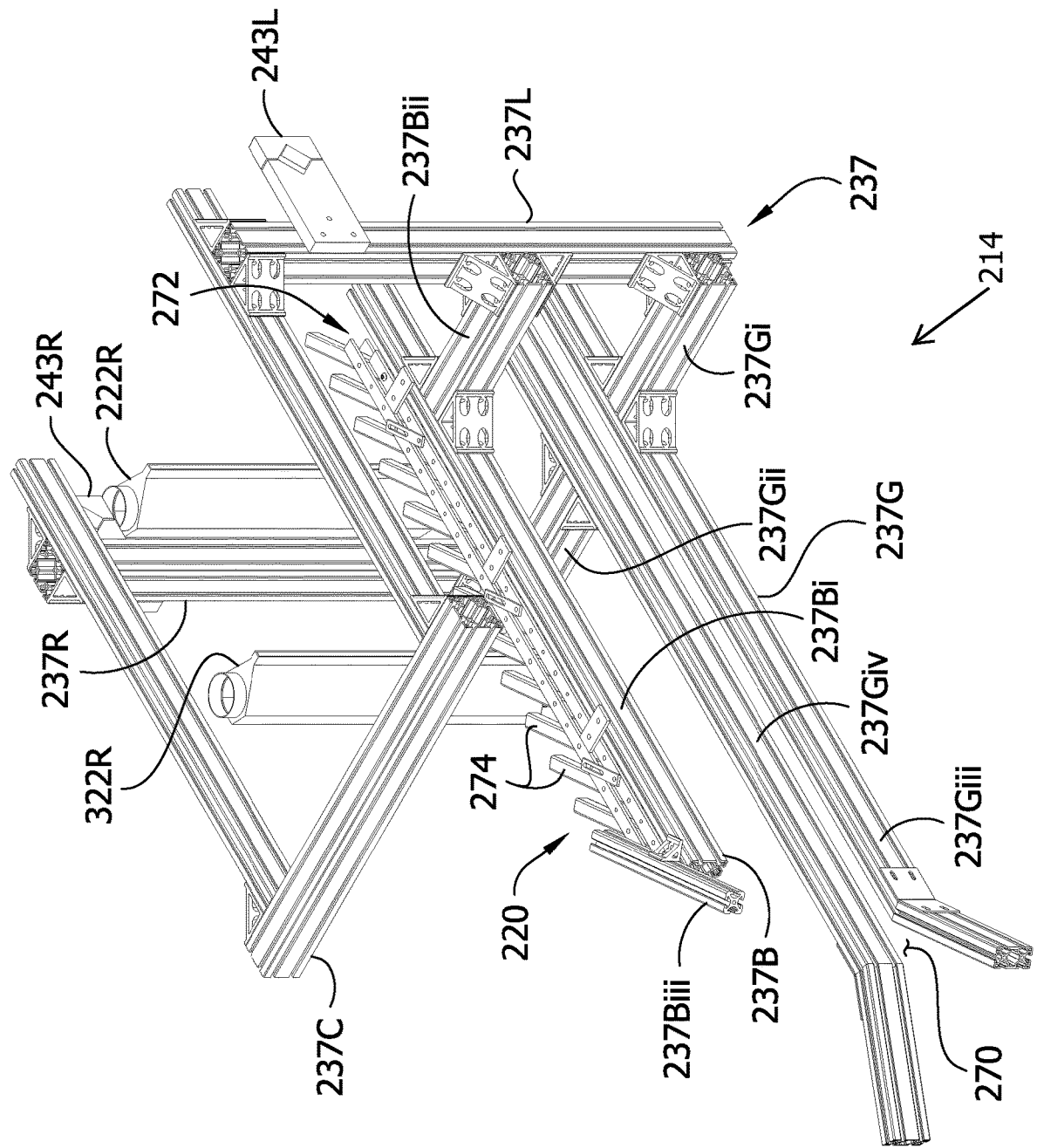
FIG. 12 is a perspective of another embodiment of a pollination unit.
Figure 13:
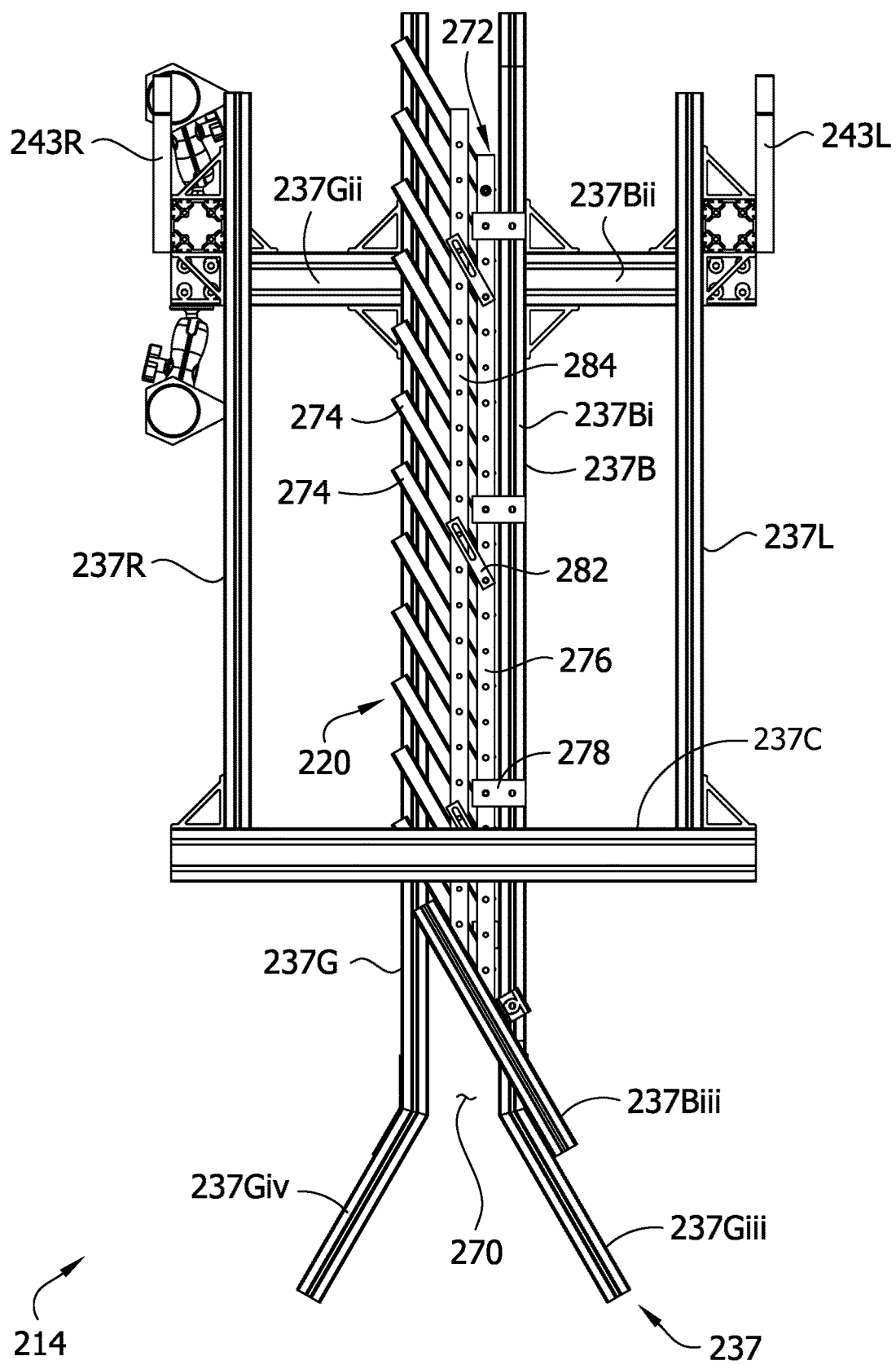
FIG. 13 is a top plan view of the pollination unit with nozzle there of FIG. 12 of removed.
Figure 14:
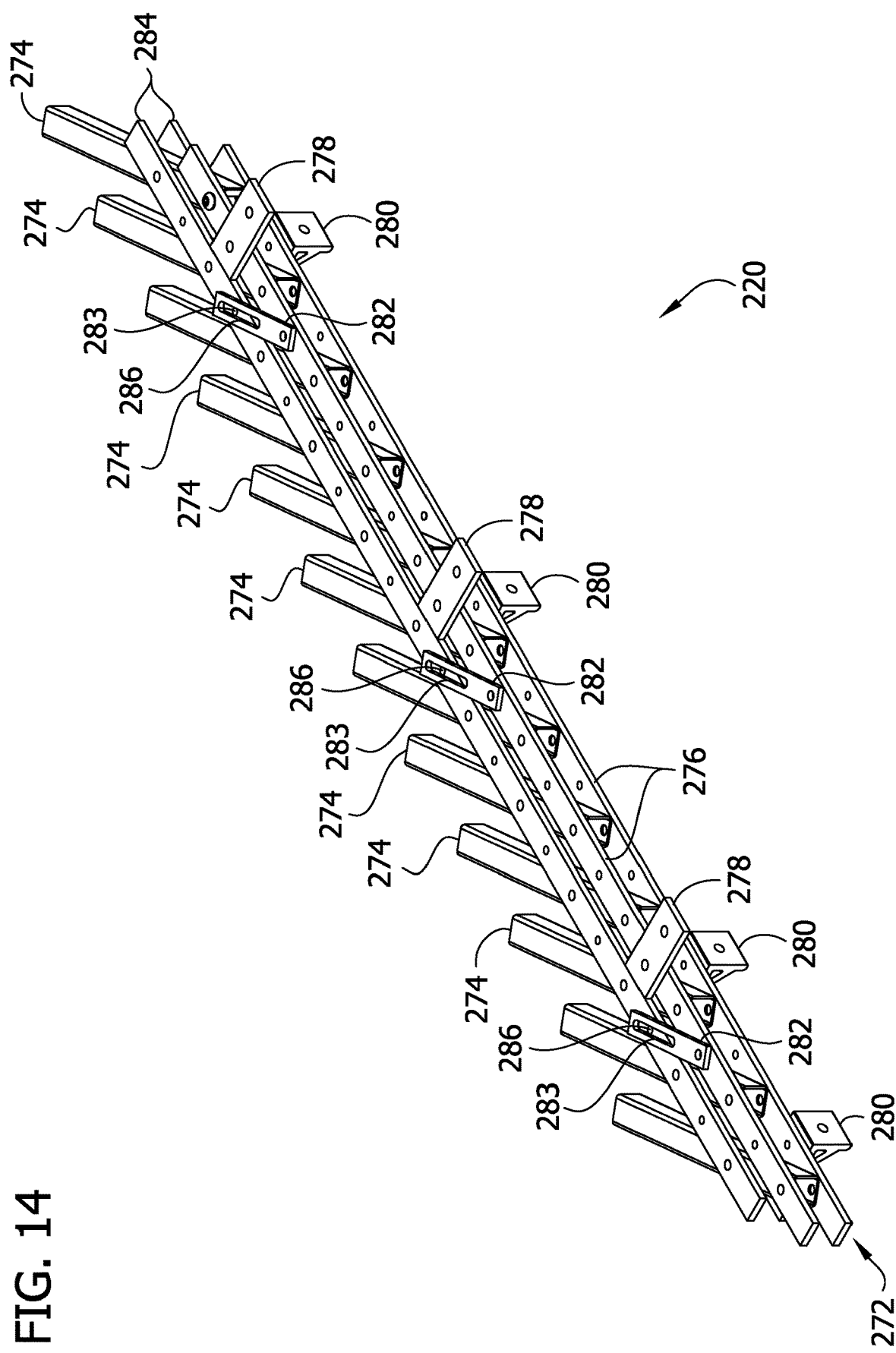
FIG. 14 is a perspective of a pollen-releasing apparatus of the pollination unit of FIG. 12.

Referring to FIGS. 12-13, in certain embodiments, one or more of the pollination units 14, 114 can be replaced with an alternative pollination unit, generally indicated at 214. The pollination unit 214 is similar in many respects to the pollination unit 14, and corresponding parts are given corresponding reference numbers, plus two-hundred. Like the pollination unit 14, the pollination unit 214 comprises an adjustable chassis 237 for mounting the pollination unit on the free end of a swing arm 34. The chassis 237 includes a left frame assembly 237L, a right frame assembly 237R, and a cross bar 237C that have generally the same features as the corresponding components 37L, 37R, 37C of the chassis 37. Left and right swing arm mounts 243L, 243R are adjustably connected to the left and right frame assemblies 237L, 237R for mounting the chassis 237 on the swing arm 34. And like the frame assemblies 37L, 37R, each of the frame assemblies 237L, 237R is configured to mount one or more air flow nozzles 222R (left air flow nozzles not shown), which may be similar or identical to prior disclosed air flow nozzles 22R, 22L, for adjusting the orientation of the air flow paths for maximizing pollen delivery. Unlike the pollination unit 14, the illustrated pollination unit 214 does not support a pollen-releasing apparatus on the cross bar 237C.

Instead, the illustrated chassis 237 includes a pollen-releasing apparatus bracket 237B that is mounted on the left frame assembly 237L. As explained below, the bracket 237B is configured to support a rigid pollen-releasing apparatus 220. Suitably, the bracket 237B is adjustable along the height of the left frame assembly 237L. The bracket 237B is generally L-shaped and includes an apparatus support member 237Bi and a connecting member 237Bii that is oriented generally perpendicular to the apparatus support member. The apparatus support member 237Bi is configured for attaching the pollen-releasing apparatus 220 to the chassis 237. The connecting member 237Bii is configured for mounting the apparatus support member on the left frame assembly 237L. The apparatus support member is spaced apart between the left and right frame assemblies 237L, 237R. The apparatus support member 237Bi extends generally along an axis, and when the pollination unit 214 is mounted on the tractor T, the axis is oriented substantially parallel to a direction of travel of the tractor. An angled crop guide member 237Biii is mounted on the front end portion of the apparatus support member 237Bi. The front end of the crop guide member 237Biii extends forward past the front end of portion of the apparatus support member 237Bi and in a lateral direction away from the pollen-releasing apparatus 220. The angle of the crop guide member 237Biii relative to the apparatus support member 237Bi can be adjusted for guiding crops toward the pollen-releasing apparatus 220 as the tractor T drives the pollination unit 214 forward through a field F.

The illustrated chassis further includes a crop guide assembly 237G mounted on the left and right frame assemblies 237L, 237R at a location spaced apart below the pollen-releasing apparatus bracket 237B. The crop guide assembly 237G includes a left support member 237Gi that is attached to the left frame assembly 237L and extends laterally inward from the left frame assembly. A right support member 237Gii is attached to the right frame assembly 237R and extends laterally inward from the right frame assembly. The left and right support members 237Gi, 237Gii can be adjustable along the height of the left and right frame assemblies 237L, 237R and/or be laterally adjustable inwardly and outwardly with respect to the left and right frame assemblies. Left and right crop guide members 237Giii, 237Giv are mounted on the laterally inner end portions of the left and right support members 237Gi, 237Gii, respectively, and are adjustable along an axis in forward and backward directions with respect to the left and right support members. The left and right support members 237Gi, 237Gii mount the left and right crop guide members 237Giii, 237Giv to define between them a guide passage 270 extending generally parallel to the forward direction of travel of the tractor T during use of the pollination unit 214. Rear end portions of the left and right crop guide members 237Giii, 237Giv extend generally parallel to the forward direction of travel of the tractor T and parallel to one another. The front end portions of the crop guide members 237Giii, 237Giv are oriented at angles to extend laterally outward away from one another as they extend forward from the rear end portions to the front end of the crop guide assembly 237G.

Thus, the crop guide assembly 237G defines a crop guide passage 270 having an opening at a front end that is wider than a rear end portion of the passage. The passage 270 tapers as it extends rearward from the wide front end portion to a rear segment that has a substantially constant, relatively narrow width. The rear segment of the passage 270 has an open rear end. During use of the pollination unit 214, as the tractor T drives forward through the field F, the front end portions of the crop guide members 237Giii, 237Giv funnel pollen-bearing crops PB in one row into the passage 270. The crop guide assembly 237G guides the crops PB through the passage 270 as the tractor T travels forward. The crop guide assembly 237G is operatively aligned with the pollen-releasing apparatus bracket 237B to position the crops for being engaged by the pollen-releasing apparatus 220 as the crops are guided through the passage 270.

Referring to FIG. 14, the pollen-releasing apparatus 220 includes an adjustable support assembly, generally indicated at 272, configured to mount the apparatus on the bracket 237B, and a plurality of pollen-releasing rods 274 that are mounted on the support assembly in parallel orientations at spaced apart locations. The support assembly 272 includes a pair of elongate mounting plates 276 that are spaced apart along a height of the pollen-releasing apparatus 220. An end portion of each of the rods 274 is received between the mounting plates 276 and is attached to the mounting plates for pivoting with respect to the mounting plates about a respective vertical pivot axis. Upper and lower mounting brackets 278, 280 are fixed to the mounting plates 276 and configured to be attached to the pollen-releasing apparatus support bar 237Bi of the bracket 237B. Suitably, the mounting brackets 278, 280 are adjustable along the length of the pollen-releasing apparatus support member 237Bi. A plurality of pivot arms 282 defining elongate slots 283 are attached to the mounting plates 276 and are adjustable by pivoting relative to the mounting plates about respective pivot axes. The support assembly 272 further includes a pair of elongate pivot control plates 284 that are spaced apart along a height of the pollen-releasing apparatus 220. Pins 286 attached to the pivot control plates 284 are slidably received in the slots 283. Thus the pivot arms 282 and the pins 286 link the pivot control plates 284 to the mounting plates 276. The rods 274 are received between the pivot control plates 284 and the pins 286 pivotably attach the rods to the pivot control plates.

To pivot the pollen-releasing rods 274 forward or backward and thereby adjust their orientations with respect to the forward direction of travel of the tractor T during use, the pivot control members 284 are moved forward or reward, respectively, with respect to the mounting members 276. Movement of the pivot control members 284 imparts pivoting of all of the rods 274 and the pivot arms 282 simultaneously with respect to the mounting members 272 about respective pivot axes that intersect the mounting members. By linking the pollen-releasing rods 274 to both the mounting members 276 and the pivot control members 284, the parallel orientation of the rods is maintained as the rods are pivoted. The pollen-releasing rods 274 have a pivoting range of motion that is limited by the sliding movement of the pins 286 within the slots 283. As the rods 274 pivot and the pivot control members 284 move relative to the mounting plates 276, the pins 286 slide through the slots 283. The ends of the range of motion are reached when the pins 286 are received in the ends of the slots 283. Suitably, the rods 274 are oriented at oblique, rearward extending angles with respect to a forward direction of travel of the tractor T through the entire range of motion.

Referring again to FIGS. 12 and 13, in use the pollination unit 214 is mounted on a pollination device base 12 and the chassis 237 is adjusted so that the pollen-releasing apparatus support bracket 237B positions the pollen-releasing apparatus 220 to engage the tassels MF of the pollen-bearing corn plants PB when the corn plants are guided through the passage 270 of the crop guide assembly 237B. As the tractor T drives the pollination units 214 forward through a field F., the crop guide assembly 237G of the chassis 237 funnels pollen-bearing plants PB in a row into the guide passage 270 and guides the plants through the length of the guide passage. As the plants PB move through the guide passage 270, their tassels MF engage the rods 274 of the pollen-releasing apparatus 220. Each of the rods 274 successively engages the tassels MF of each corn plant PB in the row and thereby releases the pollen from the tassels. Because the rods 274 are oriented at oblique, rearwardly extending angles, they strike to corn plants PB in a relatively gentle manner that limits damage to the corn plants while still releasing pollen from the tassels MF. Furthermore, because the rods 274 are rigidly mounted on the chassis 237 they remain aligned with the corn plants PB at all times while the tractor T travels along the row.

The pollination units 214 are suitably used in combination with the air handling system 16 described above. For example, the air balancing valves 50 and left and right nozzles 222R (222L not shown in FIGS. 12 and 13) can be mounted on the left and right frame assemblies 237L, 237R of the chassis 237 as they are mounted on the left and right frame assemblies 37L, 37R of the chassis 37. Thus, as explained above, the air handling system 16 can blow pollen that the rods 274 release from the tassels MF toward the stamens FF of the pollen-receiving corn plants PR to cross-pollinate the pollen-receiving corn plants with the pollen from the pollen-bearing corn plants PB.

As can be seen the pollination devices 10, 110 and pollination units 14, 114, 214 can be used to direct pollen from pollen-bearing plants PB to pollen-receiving plants PR. The pollination devices 10, 110 and units 14, 114, 214 are highly adjustable to account for different types of plants and different variations of a particular type of plant, along with changes in environmental conditions. As compared with conventional pollination techniques, using the pollination devices 10, 110 and units 14, 114, 214 is thought to increase the percentage of a field that can be planted with a pollen-receiving variety of a plant. Furthermore, the pollination devices 10, 110 and units 14, 114, 214 have been shown to increase yields in comparison with conventional pollination techniques.

For example, table 1 below shows the effect of the pollination device 110 on fields F planted with sets S of four pollen-receiving rows of corn PR and two pollen-bearing rows of corn PB (i.e., a 4×2 field) and on fields planted with sets of two pollen-receiving rows of corn and two pollen-bearing rows of corn (i.e., a 2×2 field).

TABLE 1

|  | Seeds/Ear | | Seed Bags/Hectare | |
| --- | --- | --- | --- | --- |
|  | Without Pollination Device | With Pollination Device | Without Pollination Device | With Pollination Device |
| 4 × 2 Field | 128.25 | 152.8 | 15.06 | 17.94 |
| 2 × 2 Field | 180.9 | 208.4 | 16.32 | 18.81 |

As can be seen, using the pollination device 110 had a positive impact on yields in both the 4×2 fields and the 2×2 fields. In the case of the 4×2 fields, the pollination device 110 increased the yield of seeds/cob and seed bags/hectare by more than 19%. And in the case of the 2×2 field, the pollination device 110 increased the yield of seeds/cob and seed bags/hectare by more than 15%.

Tables 2 below shows the effects of the pollination device 110 on fields F planted with sets S of four pollen receiving rows of corn PR and two pollen-bearing rows of sweet corn PB (i.e., a 4×2 field) arranged such that adjacent rows were spaced apart from one another by a distance of about 75 cm. The sample sets S in Table 2 include six varieties of cross-pollinated seed. For each sample pollinated with the pollination device 110, the pollination device was used to pollinate the set a first time when between 70% and 80% of the silks of the pollen receiving plants PR had emerged and again a second time when 100% of the silks had emerged. Samples were collected from spaced apart locations along the second and third rows of pollen-receiving plants PR between the rows of pollen-bearing plants PB. The average ambient wind during the pollination season was about 6 m/s. For seed varieties 1-4, using the pollination device 110 increased the seed yield by between about 10% and about 100% in comparison with the same variety of corn that was pollinated without the pollination device. The increase in seed yield associated with variety 5 was much larger but was likely at least partially caused by hail damage of some of the samples. Using the pollination device 110 did not increase the seed yield of variety 6, but this is believed to be due to certain flowering synchronicity issues that variety 6 exhibited.

TABLE 2

|  | Seeds/Ear | |
| --- | --- | --- |
| Variety | Without Pollination Device | With Pollination Device |
| 1 | 113 | 128 |
| 2 | 293 | 321 |
| 3 | 213 | 254 |
| 4 | 155 | 252 |
| 5 | 85 | 309 |
| 6 | 162 | 143 |

In still another example, a pollination apparatus 10 equipped with one pollination unit 214 and an air handling system including two air nozzles 22L mounted on the left frame assembly 237L at spaced apart locations in the forward direction of travel of the tractor T was used in fields F at two locations planted with sets S of eleven rows of corn including, one pollen-bearing row of corn PB, five rows of pollen-receiving corn PR, and five rows of buffer corn between the rows of pollen-receiving corn and the row of pollen-bearing corn in an adjacent set. The pollen-bearing rows of corn PB were a purple corn variety, and all other rows of corn were a yellow corn variety. Thus, cross-pollinated corn kernels on the pollen-receiving plants PR could be identified and distinguished from non-cross-pollinated kernels by their purple color.

In each of the two field locations, two control sets S and eight test sets of corn were grown, pollinated, harvested, and analyzed. To control pollination of the pollen-receiving corn plants PR in a negative control set S at each field location, the tractor T was driven along the set without blowing air through the nozzles 22L. To control pollination of the pollen-receiving plants PR in a positive control set S at each field location, sample ears of corn were hand-pollinated with pollen from the pollen-bearing plants PB.

The eight test sets S at each field location were pollinated under various conditions by driving the tractor T along each set with the pollination unit 214 operatively set to engage the tassels MF of the plants PB in the pollen-bearing row and the air handling system blowing air through the nozzles 22L toward the pollen-receiving plants PR. For a first one of the eight test sets S at each field location, the tractor T was driven once along the set with the nozzles 22L oriented to blow air at an angle 15° above horizontal when 50% of the silks FF of the pollen-receiving plants PR had emerged. For a second one of the eight test sets S, the tractor T was driven once along the set with the nozzles 22L oriented to blow air at an angle 15° below horizontal when 50% of the silks FF of the pollen-receiving plants PR had emerged. For a third one of the eight test sets S, the tractor T was driven five times along the set with the nozzles 22L oriented to blow air at an angle 15° above horizontal when 50% of the silks FF of the pollen-receiving plants PR had emerged. For a fourth one of the eight test sets S, the tractor T was driven five times along the set with the nozzles 22L oriented to blow air at an angle 15° below horizontal when 50% of the silks FF of the pollen-receiving plants PR had emerged. For a fifth one of the eight test sets S, the tractor T was driven once along the set with the nozzles 22L oriented to blow air at an angle 15° above horizontal when 80% of the silks FF of the pollen-receiving plants PR had emerged. For a sixth one of the eight test sets S, the tractor T was driven once along the set with the nozzles 22L oriented to blow air at an angle 15° below horizontal when 80% of the silks FF of the pollen-receiving plants PR had emerged. For a seventh one of the eight test sets S, the tractor T was driven five times along the set with the nozzles 22L oriented to blow air at an angle 15° above horizontal when 80% of the silks FF of the pollen-receiving plants PR had emerged. For a eighth one of the eight test sets S, the tractor T was driven five times along the set with the nozzles 22L oriented to blow air at an angle 15° below horizontal when 80% of the silks FF of the pollen-receiving plants PR had emerged.

For each of the sets S, sample ears of corn were collected from each row. Samples were collected from the middle portions of the rows, between the first and last ten plants PR in each row. The kernels from the sampled ears were shelled and sorted by color. Tables 3 and 4 below show the average number of seeds that were obtained from each ear of sampled corn from each of the rows in each of the field locations. In the tables, the row numbers increase with distance from the row of pollen-bearing plants PB in the respective set S. As indicated in Tables 3 and 4 below, using the pollination unit 214 improved seed yield in comparison with the negative control set, with the strongest positive effects being observed in Rows 1 and 2, among the test sets that were pollinated by five passes of the tractor T along the set, and among the test sets that were pollinated when 80% of the silks had emerged.

TABLE 3

Field Location 1

| Set Test Set # | Silk % | Pass-es | Nozzle Orient. | Row 1 | Row 2 | Row 3 | Row 4 | Row 5 | Row 6 |
|---|---|---|---|---|---|---|---|---|---|
| 1 | 50 | 1 | Up | 30 | 11 | 1 | 2 | 1 | 1 |
| 2 | 50 | 1 | Down | 24 | 3 | 2 | 2 | 3 | 1 |
| 3 | 50 | 5 | Up | 85 | 21 | 5 | 2 | 2 | 2 |
| 4 | 50 | 5 | Down | 74 | 21 | 4 | 3 | 3 | 2 |
| 5 | 80 | 1 | Up | 24 | 8 | 5 | 2 | 3 | 2 |
| 6 | 80 | 1 | Down | 36 | 6 | 3 | 2 | 3 | 4 |
| 7 | 80 | 5 | Up | 80 | 18 | 7 | 3 | 2 | 2 |
| 8 | 80 | 5 | Down | 83 | 30 | 5 | 4 | 2 | 1 |
| Negative Control | | | | 12 | 5 | 1 | 2 | 1 | 2 |
| Positive Control | | | | 200 | 175 | 191 | 222 | 230 | 200 |

TABLE 4

Field Location 2

| Set Test Set # | Silk % | Pass-es | Nozzle Orient. | Row 1 | Row 2 | Row 3 | Row 4 | Row 5 | Row 6 |
|---|---|---|---|---|---|---|---|---|---|
| 1 | 50 | 1 | Up | 9 | 12 | 7 | 2 | 0 | 1 |
| 2 | 50 | 1 | Down | 4 | 23 | 0 | 1 | 0 | 1 |
| 3 | 50 | 5 | Up | 65 | 35 | 21 | 22 | 6 | 12 |
| 4 | 50 | 5 | Down | 53 | 42 | 23 | 14 | 1 | 3 |
| 5 | 80 | 1 | Up | 15 | 14 | 6 | 8 | 1 | 0 |
| 6 | 80 | 1 | Down | 10 | 10 | 2 | 1 | 0 | 0 |
| 7 | 80 | 5 | Up | 83 | 70 | 66 | 35 | 7 | 3 |
| 8 | 80 | 5 | Down | 67 | 56 | 13 | 4 | 3 | 5 |
| Negative Control | | | | 5 | 3 | 2 | 0 | 0 | 2 |
| Positive Control | | | | 210 | 204 | 178 | 201 | 166 | 188 |

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A pollinating device for pollinating crop plants grown in rows including pollen-bearing rows and pollen-receiving rows, the device comprising:
   a base mountable on a carriage for traveling along the rows of crop plants;
   at least one pollination unit mounted on the base for delivering pollen from the crop plants in at least one of the pollen-bearing rows to the crop plants in a plurality of the pollen-receiving rows, the at least one pollination unit comprising:
   a pollen-releasing apparatus configured to contact male flowers of the crop plants in said at least one of the pollen-bearing rows as the carriage travels along the rows of crop plants and release pollen from the male flowers of the crop plants in said at least one of the pollen-bearing rows; and at least one nozzle adjacent the pollen-releasing apparatus, the at least one nozzle aligned for discharging air along a flow path behind the pollen-releasing apparatus and/or generally toward the male flowers of the crop plants contacted by the pollen-releasing apparatus as the carriage travels along the rows of crop plants such that the discharged air delivers at least some of the released pollen from the male flowers of the crop plants to the pollen-receiving rows of crop plants.

2. The pollinating device as set forth in claim 1, wherein the base has a width oriented transverse to a direction of travel of the carriage when the base is mounted on the carriage such that the base extends laterally outward from the carriage, the device comprising a plurality of pollination units spaced apart along the width of the base.

3. The pollinating device as set forth in claim 2, wherein the plurality of pollination units comprises at least four pollination units spaced apart along the width of the base.

4. The pollinating device as set forth in claim 1, wherein the at least one nozzle of the at least one pollination unit includes first and second nozzles.

5. The device as set forth in claim 4, further comprising at least one valve operatively coupled to the first and second nozzles for selectively coupling one of the first and second nozzles to a source of blown air.

6. The device as set forth in claim 1, wherein the nozzle is movably mounted on the base.

7. The device as set forth in claim 6, further comprising a ball joint mounting the nozzle on the base.

8. The device as set forth in claim 6, further comprising first and second ball joints mounting the nozzle on the base.

9. The device as set forth in claim 1, further comprising a swing arm pivotably mounting the at least one pollination unit on the base.

10. The device as set forth in claim 1, wherein the nozzle comprises an air knife.

11. The device as set forth in claim 1, further comprising a blower operatively connected to the nozzle to provide blown air to the nozzle.

12. The device as set forth in claim 11, wherein the blower is configured to provide the blown air to the nozzle such that the discharged air exits the nozzle at least at about 30 miles per hour.

13. The device as set forth in claim 11, further comprising a filter coupled to an intake of the blower for filtering intake air as it is drawn into the blower.

14. The device as set forth in claim 1, wherein the pollen-releasing apparatus comprises a chain suspended from the base.

15. The device as set forth in claim 1, wherein the pollen-releasing apparatus comprises at least one rod extending at an oblique angle with respect to a direction of travel of the carriage.

16. The device as set forth in claim 15, wherein the at least one rod comprises a plurality of rods oriented generally parallel to one another.

17. The device as set forth in claim 1, wherein the pollen-releasing apparatus comprises a crop guide assembly defining a guide passage for receiving crop plants extending generally parallel to a direction of travel of the carriage.

18. The device as set forth in claim 17, wherein the crop guide assembly is operatively aligned with the pollen-releasing apparatus to guide crop plants received in the guide passage so that the male flowers thereof contact the pollen-releasing apparatus as the carriage travels along the rows of crop plants.

19. The device as set forth in claim 18, wherein the crop guide assembly has a front end portion defining a front opening of the guide passage that is wider than a rear end portion of the guide passage.

20. The pollinating device as set forth in claim 1, wherein the pollen-releasing apparatus is configured to release the pollen from the male flowers of the crop plants in said at least one of the pollen-bearing rows into an ambient environment around the crop plants in said at least one of the pollen-bearing rows; and wherein the at least one nozzle is configured to discharge air along the flow path to blow at least some of the pollen in the ambient environment to the pollen-receiving rows of crop plants.

21. A device for pollinating crop plants grown in rows including pollen-bearing rows and pollen-receiving rows, the device comprising:

a base mountable on a carriage for traveling in a travel direction oriented parallel to the rows of crop plants, the base having a width and being configured for being mounted on the carriage such that the width is oriented transverse to the travel direction;

a pollen blowing system comprising:

at least one blower configured to provide blown air;

a filter coupled to an intake of the blower for filtering intake air as it is drawn into the blower; and a plurality of nozzles mounted on the base at spaced apart positions along the width of the base corresponding with a spacing of the pollen-bearing rows of the rows of crop plants, the nozzles being configured to receive the blown air from the at least one blower and to discharge the blown air toward the crop plants in respective ones of the pollen-bearing rows to deliver pollen from the crop plants in the pollen-bearing rows to the crop plants in the pollen-receiving rows as the carriage travels along the crop plants; and a crop guide assembly disposed adjacent at least one of the plurality of nozzles, the crop guide assembly defining a guide passage for receiving the crop plants in the pollen-bearing rows and directing the received crop plants toward the blown air discharged from the at least one of the plurality of nozzles, wherein a front opening of the guide passage is wider than a rear opening of the guide passage.

22. A pollinating device for pollinating crop plants grown in rows including pollen-bearing rows and pollen-receiving rows, the device comprising:

a base mountable on a carriage for traveling along the rows of crop plants;

at least one pollination unit mounted on the base for delivering pollen from the crop plants in at least one of the pollen-bearing rows to the crop plants in a plurality of the pollen-receiving rows, the at least one pollination unit comprising:

a pollen-releasing apparatus configured to contact male flowers of the crop plants in said at least one of the pollen-bearing rows as the carriage travels along the rows of crop plants and release pollen from the male flowers of the crop plants in said at least one of the pollen-bearing rows, the pollen-releasing apparatus including a chain; and at least one nozzle adjacent the pollen-releasing apparatus for discharging air along a flow path as the carriage travels along the rows of crop plants such that the discharged air delivers at least some of the released pollen to the pollen-receiving rows of crop plants.

23. A pollinating device for pollinating crop plants grown in rows including pollen-bearing rows and pollen-receiving rows, the device comprising:
- a base mountable on a carriage for traveling along the rows of crop plants;
- at least one pollination unit mounted on the base for delivering pollen from the crop plants in at least one of the pollen-bearing rows to the crop plants in a plurality of the pollen-receiving rows, the at least one pollination unit comprising:
  - a pollen-releasing apparatus configured to contact male flowers of the crop plants in said at least one of the pollen-bearing rows as the carriage travels along the rows of crop plants and release pollen from the male flowers of the crop plants in said at least one of the pollen-bearing rows;
  - a crop guide assembly defining a guide passage for receiving crop plants extending generally parallel to a direction of travel of the carriage, wherein a front opening of the guide passage is wider than a rear opening of the guide passage, and wherein the crop guide assembly is operatively aligned with the pollen-releasing apparatus to guide crop plants received in the guide passage so that the male flowers thereof contact the pollen-releasing apparatus as the carriage travels along the rows of crop plants; and
  - at least one nozzle adjacent the pollen-releasing apparatus for discharging air along a flow path as the carriage travels along the rows of crop plants such that the discharged air delivers at least some of the released pollen to the pollen-receiving rows of crop plants.

24. A pollinating device for pollinating crop plants grown in rows including pollen-bearing rows and pollen-receiving rows, the device comprising:
- a base mountable on a carriage for traveling along the rows of crop plants;
- at least one pollination unit mounted on the base for delivering pollen from the crop plants in at least one of the pollen-bearing rows to the crop plants in a plurality of the pollen-receiving rows, the at least one pollination unit comprising:
  - a pollen-releasing apparatus configured to contact male flowers of the crop plants in said at least one of the pollen-bearing rows as the carriage travels along the rows of crop plants and release pollen from the male flowers of the crop plants in said at least one of the pollen-bearing rows; and
  - at least one nozzle adjacent the pollen-releasing apparatus for discharging air along a flow path as the carriage travels along the rows of crop plants such that the discharged air delivers at least some of the released pollen to the pollen-receiving rows of crop plants;
- a blower operatively connected to the at least one nozzle to provide blown air to the at least one nozzle; and
- a filter coupled to an intake of the blower for filtering intake air as it is drawn into the blower.

* * * * *